US011571471B2

(12) United States Patent
Steigerwald et al.

(10) Patent No.: US 11,571,471 B2
(45) Date of Patent: *Feb. 7, 2023

(54) RECOMBINANT MODIFIED VACCINIA VIRUS ANKARA (MVA) EQUINE ENCEPHALITIS VIRUS VACCINE

(71) Applicant: Bavarian Nordic A/S, Hellerup (DK)

(72) Inventors: Robin Steigerwald, Munich (DE); Markus Kalla, Penzberg (DE)

(73) Assignee: Bavarian Nordic A/S, Hellerup (DK)

( * ) Notice: Subject to any disclaimer, the term of this patent is extended or adjusted under 35 U.S.C. 154(b) by 0 days.

This patent is subject to a terminal disclaimer.

(21) Appl. No.: 17/140,357

(22) Filed: Jan. 4, 2021

(65) Prior Publication Data

US 2021/0205439 A1    Jul. 8, 2021

Related U.S. Application Data

(63) Continuation of application No. 16/073,434, filed as application No. PCT/EP2017/051807 on Jan. 27, 2017, now Pat. No. 10,881,725.

(30) Foreign Application Priority Data

Jan. 29, 2016 (EP) .................... 16153394
Feb. 24, 2016 (EP) .................... 16157055
Aug. 19, 2016 (EP) .................... 16185012

(51) Int. Cl.
| | | |
|---|---|---|
| *C12N 15/863* | (2006.01) | |
| *A61K 39/15* | (2006.01) | |
| *A61K 39/12* | (2006.01) | |
| *C12N 15/86* | (2006.01) | |
| *C07K 14/005* | (2006.01) | |
| *A61P 31/14* | (2006.01) | |
| *C12N 7/00* | (2006.01) | |
| *A61K 39/00* | (2006.01) | |

(52) U.S. Cl.
CPC .............. *A61K 39/15* (2013.01); *A61K 39/12* (2013.01); *A61P 31/14* (2018.01); *C07K 14/005* (2013.01); *C12N 7/00* (2013.01); *C12N 15/86* (2013.01); *A61K 2039/5254* (2013.01); *A61K 2039/5256* (2013.01); *A61K 2039/545* (2013.01); *C12N 2710/24134* (2013.01); *C12N 2710/24143* (2013.01); *C12N 2710/24171* (2013.01); *C12N 2720/12134* (2013.01); *C12N 2720/12143* (2013.01); *C12N 2720/12171* (2013.01); *C12N 2770/36134* (2013.01)

(58) Field of Classification Search
CPC ... C12N 15/86; C12N 2830/00; A61K 39/275
See application file for complete search history.

(56) References Cited

U.S. PATENT DOCUMENTS 10,881,725 B2 * 1/2021 Steigerwald ......... C07K 14/005

FOREIGN PATENT DOCUMENTS

| WO | 2002/018585 A2 | 3/2002 |
|---|---|---|
| WO | 2002/042480 A2 | 5/2002 |
| WO | 2003/097845 A1 | 11/2003 |
| WO | 2005/003363 A1 | 1/2005 |
| WO | 2006/041897 A2 | 4/2006 |
| WO | 2008/101349 A1 | 8/2008 |
| WO | 2014/063832 A1 | 5/2014 |

OTHER PUBLICATIONS

Wu et al., "Complete protection of mice against a lethal dose challenge of western equine encephalitis virus after immunization with an adenovirus-vectored vaccine," Vaccine, 2007, pp. 4368-4375, vol. 25.
Griffin, "Alphaviruses," Chapter 23 in Fields Virology, 6th ed., 2013, pp. 651-662 (Lippincott, Williams, & Wilkins).
Carossino et al., "Novel vaccination approaches against equine alphavirus encephalitides," Vaccine, 2014, pp. 311-319, vol. 32.
Phillpotts et al., "Intranasal immunisation with defective adenovirus serotype 5 expressing the Venezuelan equine encephalitis virus E2 glycoprotein protects against airborne challenge with virulent virus," Vaccine, 2005, pp. 1615-1623, vol. 23.
Kim et al., "New world and old world alphaviruses have evolved to exploit different components of stress granules, FXR and G3BP proteins, for assembly of viral replication complexes," PLOS Pathogens, 2016, DOI: 10.1371/journal.opat.1005810.
Garcia-Arriaza et al., "A Novel Poxvirus-Based Vaccine, MVA-CHIKV, Is Highly Immunogenic and Protests Mice against Chikungunya Infection," Journal of Virology, 2014, pp. 3527-3547, vol. 88.
Volz et al., "Protective efficacy of Modified Vaccinia virus Ankara in preclinical studies," Vaccine, 2013, pp. 4235-4240, vol. 31.
Gomez et al., "MVA and NYVAC as Vaccines against Emergent Infectious Diseases and Cancer," Current Gene Therapy, 2011, pp. 189-217, vol. 11.
Sanchez-Puig et al., "A Vaccinia Virus Recombinant Transcribing an Alphavirus Replicon and Expressing Alphavirus Structural Proteins Leads to Packaging of Alphavirus Infectious Single Cycle Particles," PLOS ONE, 2013, e275574, vol. 8.

(Continued)

*Primary Examiner* — Bao Q Li

(57) ABSTRACT

The present invention relates to recombinant modified vaccinia virus Ankara (MVA) and to methods of using the same. In particular, the invention relates to recombinant MVA comprising a nucleotide sequence encoding for a structural protein of an equine encephalitis virus (EEV) excluding encoding for a capsid protein of the EEV, a composition in particular a pharmaceutical composition, a vaccine or kit comprising the recombinant MVA, uses and methods thereof e.g., suitable for treating and/or preventing a western, Venezuelan, and/or eastern equine encephalitis virus caused disease.

20 Claims, 12 Drawing Sheets

Specification includes a Sequence Listing.

(56) References Cited

OTHER PUBLICATIONS

Vasilakis et al., "Transfection-independent production of alphavirus replicon particles based on poxvirus expression vectors," Nature Biotechnology, 2003, pp. 932-935, vol. 21.
Phillpotts et al., "Vaccinia virus recombinants encoding the truncated structural gene region of Venezuelan equine encephalitis virus (VEEV) give solid protection against peripheral challenge but only partial protection against airborne challenge with virulent VEEV," Acta Virologica, 2000, pp. 233-239, vol. 44.
Written Opinion and Search Report of the International Search Authority for PCT/EP2017/051807 dated May 30, 2017.
Leung et al., "Replication of alphaviruses: a review on the entry process of alphaviruses into cells," Advances in Virology, 2011, Article ID 249640, vol. 2011.
Bourai et al., "Mapping of chikungunya virus interactions with host proteins identified nsP2 as a highly connected viral component," J. Virol., 2012, pp. 3121-3134, vol. 86.
Nagata et al., "Vaccines and therapeutics for the encephalitic alphaviruses," Future Virology, 2013, pp. 661-674, vol. 8.
Kinney et al., "Recombinant Vaccinia Virus/ Venezuelan Equine Encephalitis (VEE) Virus Protects Mice from Peripheral VEE Virus Challenge," J. Virol., 1988, pp. 4697-4702, vol. 62.
Weger-Lucarelli et al., "A Novel MVA Vectored Chikungunya Virus Vaccine Elicits Protective Immunity in Mice," PLOS Neglected Tropical Diseases, 2014, pp. 1-14, vol. 8, e2970.

* cited by examiner

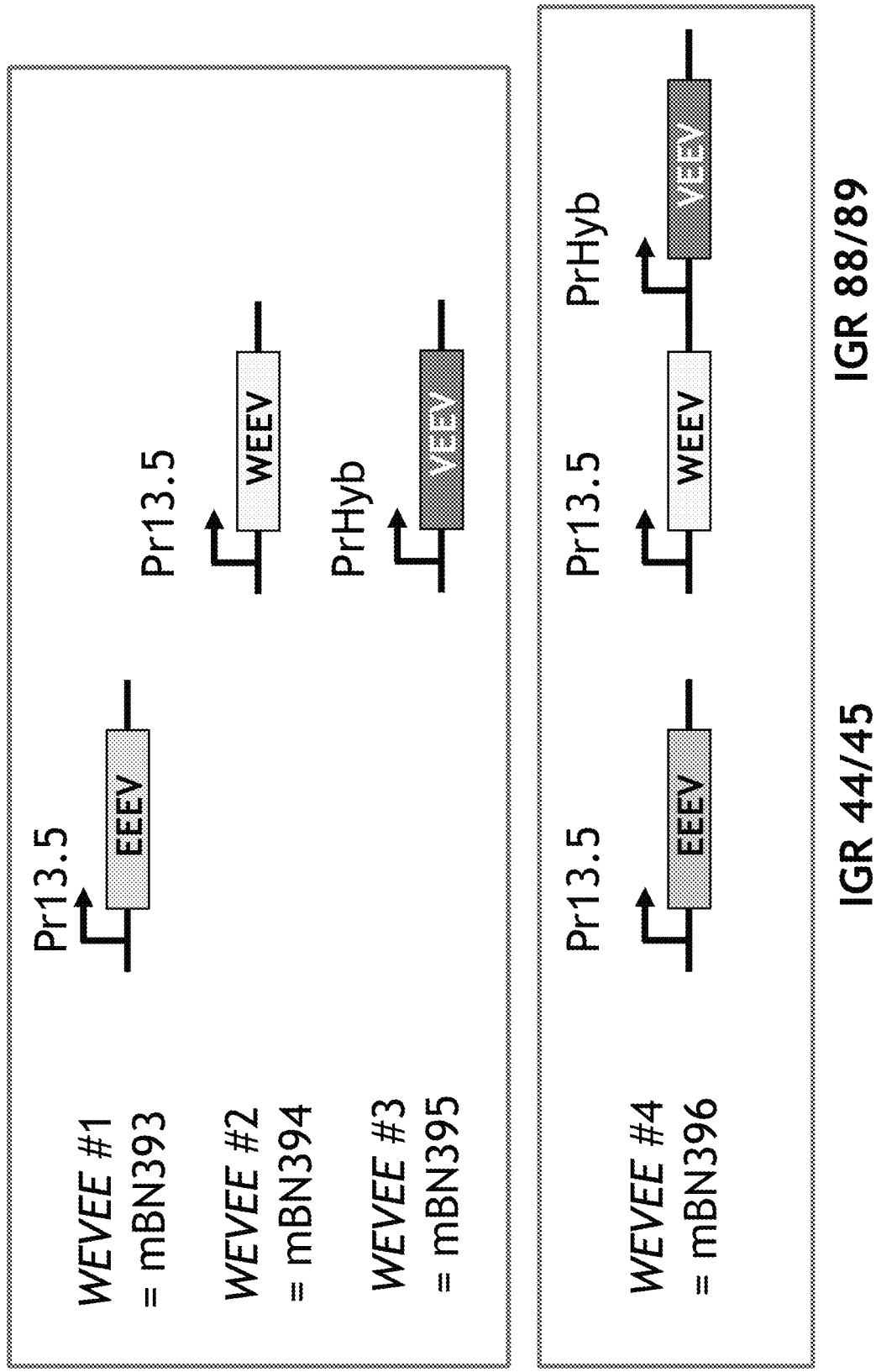

Fig. 2A

WEEV
(71V-1658)

Fig. 2B

EEEV (PE-6)

VEEV (TrD)

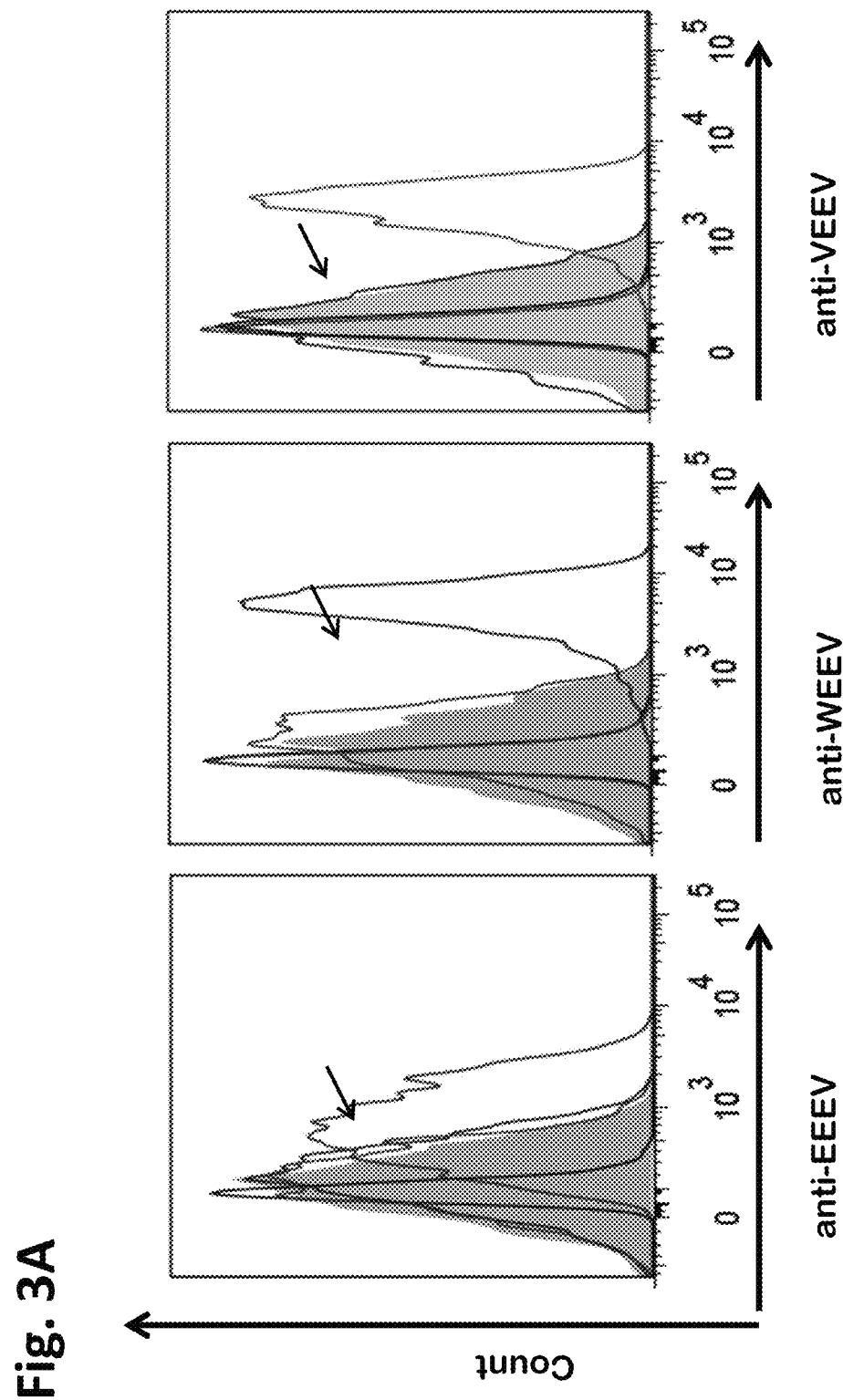

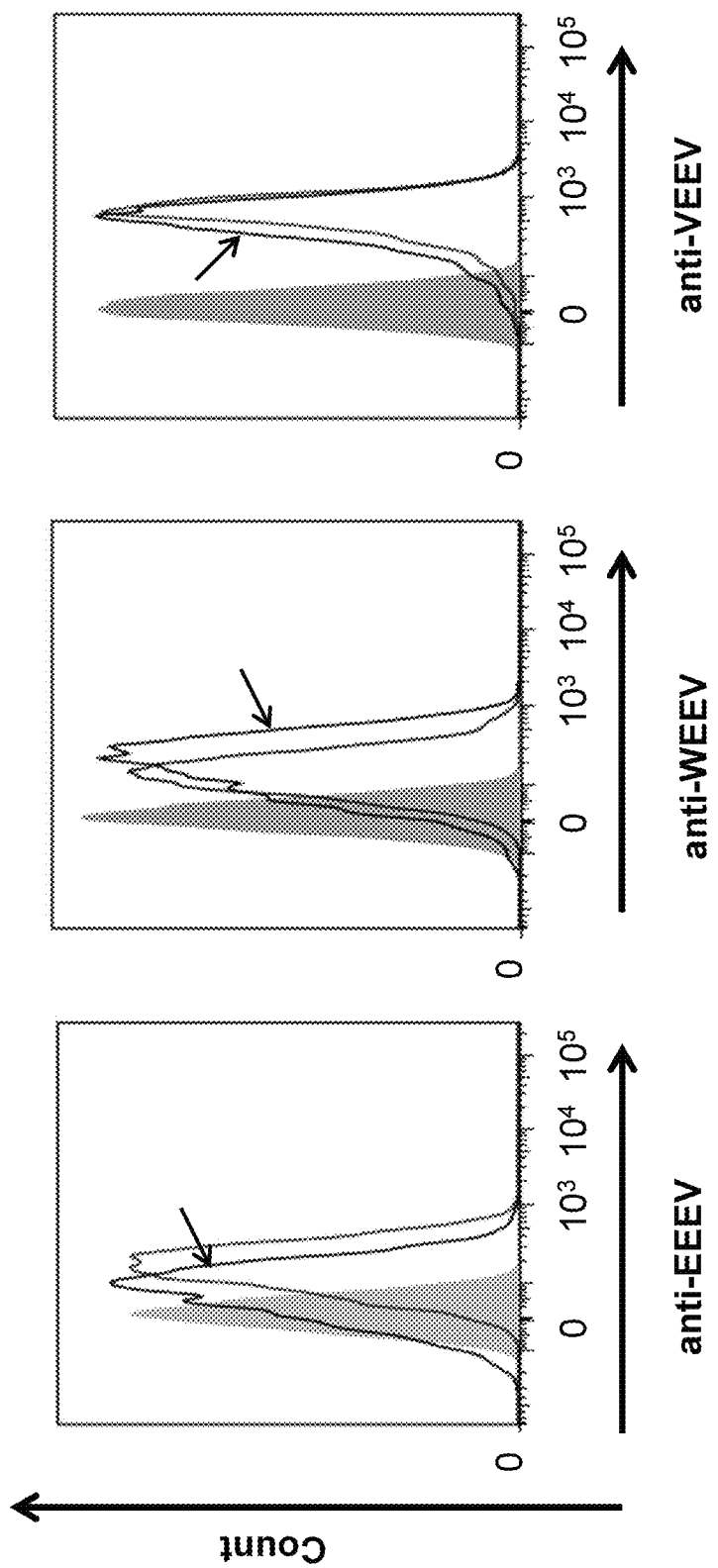

| Vaccines | Immun. routes | Neutralizing titers | | |
|---|---|---|---|---|
| | | Pre-serum | 14 days | 41 days |
| MVA-BN-VEEV | S.C. | <60 | <60 | 2,160 |
| MVA-BN-VEEV | I.M. | <60 | <60 | > 6,480 |
| Mixture of 3 Vaccines | S.C. | <60 | <60 | <60 |
| MVA-BN | S.C. | <60 | <60 | <60 |

Fig. 5A

| Vaccines | Strains | Neutralizing titers | | |
|---|---|---|---|---|
| | | Pre-serum | 14 days | 41 days |
| MVA-BN-WEEV | 71V | <60 | 180 | 360 |
| Mixture of 3 Vaccines | 71V | <60 | 60 | 180 |
| MVA-BN | 71V | <60 | <60 | <60 |
| MVA-BN-WEEV | Fleming | <60 | 180 | 720 |
| Mixture of 3 Vaccines | Fleming | <60 | 60 | 360 |
| MVA-BN | Fleming | <60 | <60 | <60 |

Fig. 5B

| Vaccines | Neutralizing titers | | |
|---|---|---|---|
| | Pre-serum | 14 days | 41 days |
| MVA-BN-EEEV | <60 | 60 | 720 |
| Mixture of 3 Vaccines | <60 | <60 | 180 |
| MVA-BN | <60 | <60 | <60 |

Fig. 5C

| Vaccines | Immun. routes | Survival rates (survival/total) | | |
|---|---|---|---|---|
| | | Challenge strains | Challenge doses (pfu) | |
| | | | $5 \times 10^3$ | $10^4$ |
| MVA-BN-EEEV | S.C. | PE6 | 5/5 | |
| Mixture of 3 Vaccines | S.C. | PE6 | 3/5 | |
| MVA-BN | S.C. | PE6 | 0/5 | |
| MVA-BN-WEEV | S.C. | 71V | 4/5 | |
| MVA-BN | S.C. | 71V | 0/5 | |
| MVA-BN-WEEV | S.C. | Fleming | 5/5 | |
| Mixture of 3 Vaccines | S.C. | Fleming | 5/5 | |
| MVA-BN | S.C. | Fleming | 0/5 | |
| MVA-BN-VEEV | S.C. | TrD | 5/5 | 5/5 |
| MVA-BN-VEEV | I.M. | TrD | | 5/5 |
| Mixture of 3 Vaccines | S.C. | TrD | 5/5 | |
| MVA-BN | S.C. | TrD | 0/5 | 0/5 |

| | | | |
|---|---|---|---|
| MVA-BN trivalent | S.C. | TrD | 4/5 |

Figure 6

| Vaccine | Challenge Strain (IN) | Challenge Dose | Efficacy |
|---|---|---|---|
| MVA-BN-VEEV | VEEV TrD | 10⁴ PFU | 100% (5/5) |
| | VEEV TrD | 5x10³ PFU | 100% (20/20) |
| | VEEV TrD | 10³ PFU | 100% (4/4) |
| | WEEV 71V-1658 | 10⁴ PFU | 100% (5/5) |
| | WEEV 71V-1658 | 5x10³ PFU | 80 % (4/5) |
| MVA-BN-WEEV | WEEV 71V-1658 | 10³ PFU | 100 % (5/5) |
| | WEEV Fleming** | 5x10³ PFU | 90% (9/10) |
| | EEEV PE-6** | 10⁴ PFU | 75% (3/4) |
| MVA-BN-EEEV | EEEV PE-6** | 5x10³ PFU | 80% (8/10) |
| | EEEV PE-6** | 10³ PFU | 100% (5/5) |
| MVA-BN-W/E/VEEV Triple Mix | VEEV TrD | | 100% (15/15) |
| | WEEV 71V-1658 | 5x10³ PFU | 80% (4/5) |
| | WEEV Fleming** | | 100% (5/5) |
| | EEEV PE-6** | | 60% (3/5) |
| MVA-BN-trivalent (mBN396) | VEEV TrD (1/3 dose) | 5x10³ PFU | 80% (8/10) |

Figure 7

RECOMBINANT MODIFIED VACCINIA VIRUS ANKARA (MVA) EQUINE ENCEPHALITIS VIRUS VACCINE

FIELD OF THE INVENTION

The present invention relates to a recombinant modified vaccinia virus Ankara-based (MVA-based) vaccine against equine encephalitis virus in particular western (WEEV), Venezuelan (VEEV) and/or eastern equine encephalitis virus (EEEV) infection and to related products, methods and uses. Specifically, the present invention relates to genetically engineered (recombinant) MVA vectors comprising structural proteins of those viruses in particular comprising E3, E2, 6k and E1, preferably excluding sequences encoding for a capsid protein. The invention also relates to products, methods and uses thereof, e.g., suitable to induce a protective immune response in a subject.

BACKGROUND OF THE INVENTION

Venezuelan (VEEV), Eastern (EEEV), and Western Equine Encephalitis viruses (WEEV), members of the genus Alphavirus in the family of Togaviridae, are causative agents of deliberative, acute, and sometimes fatal encephalitis (Spurgers K. B. and Glass P. J. (2011), J Bioterr. & Biodef S1:001-9). These viruses are maintained in nature in alternating cycles between mosquito vectors and the natural reservoir of wild birds, while they occasionally become zoonotic and are transmitted via mosquitos to humans and horses, which are tangential dead end hosts. Natural human diseases are rare but like the North American EEEV isolates are highly virulent, being the most deadly mosquito-borne pathogen in North-America with a fatality rate estimated at 35 to 75% (Yu et al. (2015), Genome Announc. 3: e00243-15). The case fatality rate for WEEV has been estimated to be about 10% for humans and 20% for equines. In humans, EEEV and WEEV are neurotropic viruses that produce limited viremia followed by CNS infection across the cerebral vascular endothelium or the olfactory epithelium, whereas VEEV causes encephalitis in less than 5% and shows a mortality rate of approximately 1% (Nagata et al. (2013), Future Virol. 8:661-674). Because of their potential to be weaponized, WEEV, EEEV and VEEV are classified as category B pathogens by the Centre for Diseases Control and Prevention (CDC) and the National Institutes of Health (NIH). So far only inactivated alphavirus vaccines preparations are used to control animal infections in endemic areas and unlicensed, investigational vaccines are in use to protect at risk-people including laboratory personal. No approved vaccines are available for general vaccination against infection of WEEV, VEEV, or EEEV.

Investigational vaccines include TC-83 and C-84 (Spurgers K. B. and Glass P. J. (2011), J Bioterr. & Biodef. S1:001-9). TC-83 is a live attenuated virus generated by serial passages of VEEV Trinidad (TrD) strain in guinea pig heart cells. Personnel at risk of exposure to VEEV are immunized with live-attenuated TC-83 as an Investigational New Drug followed by booster vaccination with formalin-inactivated C-84 if required (Nagata et al. (2013), Future Virol. 8:661-674). TC-83 vaccine is only immunogenic in approximately 80% of human recipients and approximately 40% of immunized subjects develop moderate flu-like symptoms. However, concern of side effects and reversion to the virulence of wild-type viruses is a hurdle for human treatment. Inactivated virus vaccines for EEEV and WEEV are also in use but similar to C-84 are poorly immunogenic and require frequent boosting.

Based on the nonhuman primate data TC-83 and C-84 as well as human cases of VEEV infection in previously vaccinated individuals, none of the current vaccines offers a good protection against aerosol exposure (Reed et al. (2014), Journal of Virology 88:12077-12086).

Several approaches have been used to develop safer and more efficient vaccines. V3526, that harbors a deletion of the furin cleavage site and a secondary mutation at codon 253 of E1, has proven to be highly efficient but clinical development has been stopped due to unacceptable clinical signs in humans (Spurgers K. B. and Glass P. J. (2011), J Bioterr. & Biodef. S1:001-9).

Other approaches were directed to chimeric vaccines based on a Sindbis virus (SINV) backbone which produces live attenuated virus vaccine SINV/WEEV candidates. However, despite promising vaccination results, some chimeras were highly pathogenic when administered to suckling mice, leaving concerns about safety of the vaccine.

Another approach of DNA vaccination, which requires injection of plasmid DNA encoding for proteins, has been analyzed but is less suitable for human vaccination. Nagata et al. have shown that the DNA vaccine pVHX6 did only protect 50 to 62% in mice against Fleming and CBA87 as a challenge strain via the intranasal route (Nagata et al. (2005), Vaccine 23:2280-3, U.S. Pat. Nos. 6,800,289 and 7,223,409). In addition, three injections and application with a gene gun were required. Gauci et al. tested different portions of the structural proteins of WEEV for their efficacy in a mouse model (Gauci et al. (2010), Clinical and Vaccine Immunology 17:176-179).

DNA vaccines against VEEV have been analyzed against aerosol challenge in cynomolgus macaques and/or mice by intramuscular electroporation (Dupuy et al. (2011), Vaccine Immunol. 18:707-716; Dupuy et al. (2010), Vaccine 28:7345-7350; WO 2013/151567).

Viral vectors of several types engineered to express a transgene of interest upon transduction of target cells have been widely used. Several studies have demonstrated protection of adenovirus based vectors against WEEV challenge in mice (Wu et al. (2007), Vaccine 25:4368-4375; Barabé et al. (2007), Vaccine 25:6271-6276; Swayze et al. (2011), Vaccine 29: 813-820). In WO 2008/101349 envelope proteins of WEEV 71V-1658 in Ad5 either alone or upon co-administration of Ad5-mIFNa and Ad5-WEEV has shown protection. However, pre-existing immunity to adenovirus vector in the human population could reduce the efficacy of the vaccine and is thus a major hurdle for a widespread utility of this approach. An adenovirus vector expressing E3-E2-6K structural proteins of VEEV used in an i.n. challenge model showed protection against homologous aerosol challenge but protected only partially against enzootic strains (Phillpotts et al. (2005), Vaccine 23:1615-1623).

Recombinant vaccinia virus has also been used as a vaccine to express structural VEEV proteins (Kinney et al. (1988), J. Virol. 62:4697-4702; Mathews et al. (1994), Vaccine 12:620-624; Bennett et al. (1998), Viral. Immunol. 11:109-117; Phillpotts R. J, Lescott T. L., Jacobs S. C. (2000), Acta Virol. 44:233-239; U.S. Pat. No. 6,565,853; WO 99/50292). While these vaccines are efficacious in mice against peripheral infection, they fail to offer full protection against intranasal or aerosol VEEV exposure. U.S. Pat. No. 6,936,257 (WO 99/63098) discloses a vaccinia virus expressing a modified structural protein of VEEV which only protected up to 60% of mice.

Viral replicon particle (VRP) vaccines have been described but very high doses were required to protect NHPs (Reed et al. (2014), J Virol. 88:12077-86).

An additional concern of alphavirus vaccine is cross-interference with other alphavirus vaccines and interference among WEEV, VEEV and EEEV vaccines, thus the development of vaccines that confer protection without immune interference is a goal of alphavirus vaccine strategies (Phillips et al. (2014), J Virol. 88:1771-1780).

In the absence of a suitable vaccine, there is a need to overcome the disadvantages for developing safe and more effective vaccines and therapeutics that protect against WEEV, VEEV, and/or EEEV infection and/or protection of humans to be effective in a biodefense scenario in particular against an respiratory or aerosol route of exposure.

BRIEF SUMMARY OF THE INVENTION

One aspect of the present invention provides a recombinant modified vaccinia virus Ankara (MVA) comprising a nucleotide sequence of a poxvirus promoter operably linked to a nucleotide sequence encoding for a structural protein of an equine encephalitis virus (EEV) excluding encoding for a capsid protein of the EEV.

Another aspect of the invention relates to a composition comprising the recombinant MVA of the present invention and a pharmaceutical acceptable carrier, excipient, or vehicle.

Another aspect of the invention relates to a vaccine, and/or cell comprising the recombinant MVA of the present invention.

Another aspect of the invention relates to a kit comprising the recombinant MVA, and/or the composition, and/or the vaccine comprising the recombinant MVA of the present invention in a first vial or container for a first administration (priming) and in a second vial or container for a second administration (boosting).

Another aspect of the present invention relates to a recombinant MVA of the present invention, and/or the composition, and/or the vaccine comprising the recombinant MVA of the present invention for use as a medicament or vaccine.

Another aspect of the present invention relates to a recombinant MVA of the present invention, and/or the composition, and/or the vaccine comprising the recombinant MVA of the present invention for manufacturing of a vaccine for treating and/or preventing an equine encephalitis virus caused disease, preferably a Venezuelan, western and/or eastern equine encephalitis virus caused disease.

Another aspect of the invention relates to the use of the recombinant MVA, the pharmaceutical composition, or the vaccine of the present invention for manufacturing of a vaccine for treating and/or preventing an equine encephalitis virus caused disease.

Another aspect of the invention relates to a method for affecting an immune response in a subject comprising administering to the subject the recombinant MVA, the pharmaceutical composition, or the vaccine of the present invention.

Another aspect of the invention relates to a method for treating and/or preventing in a subject an equine encephalitis virus caused disease comprising administering to the subject the recombinant MVA, the pharmaceutical composition, or the vaccine of the present invention.

These and other objects of the invention will be described in further detail in connection with the detailed description of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 1 illustrates the design of recombinant MVA of the invention expressing EEV structural polyproteins E3-E2-6k-E1. As insertion sites IGR 44/45 (EEEV) and IGR 88/89 (WEEV and VEEV) were used according to the position as described in WO 03/097845.

Figure 2A:
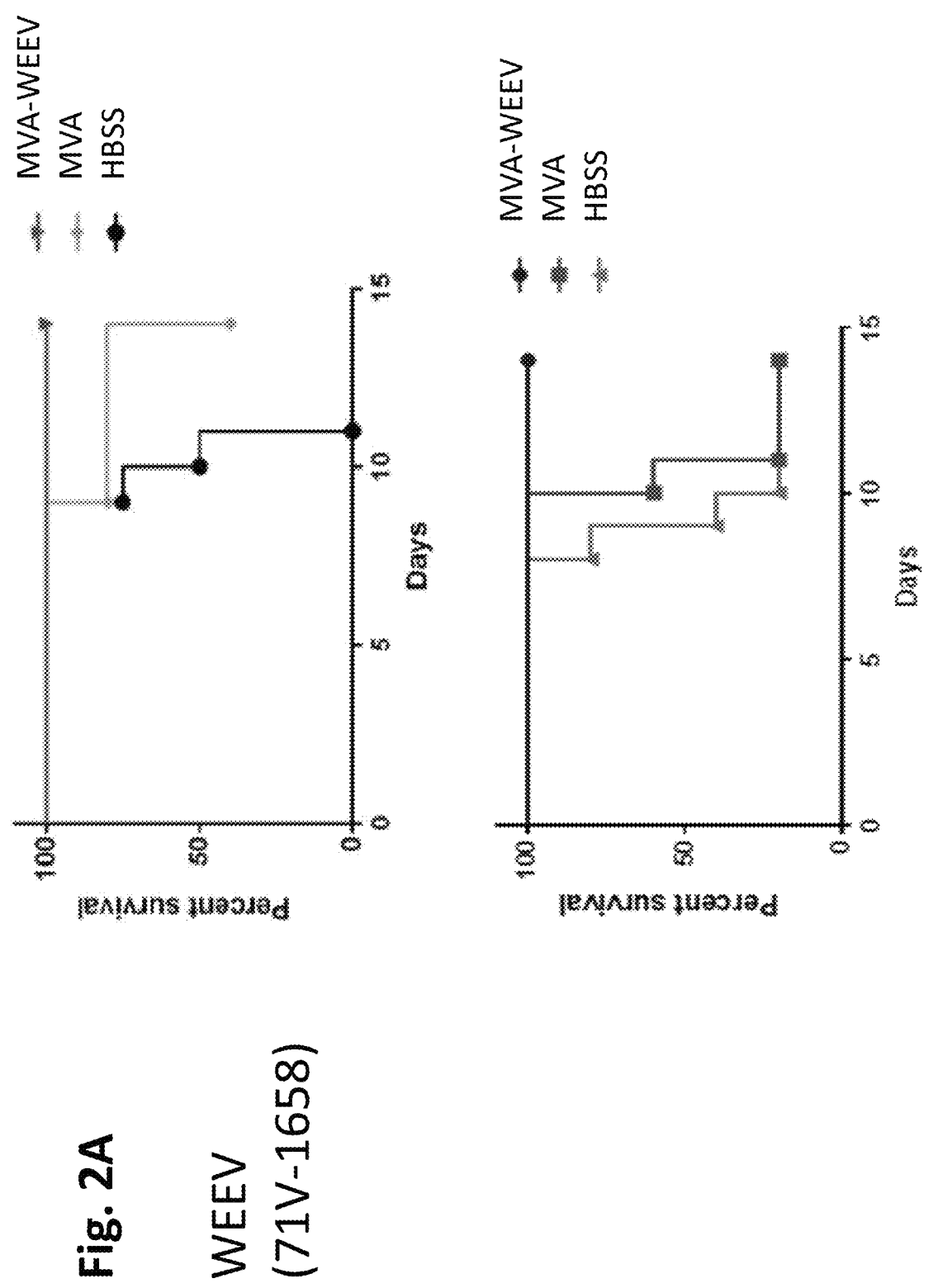
Figure 2B:
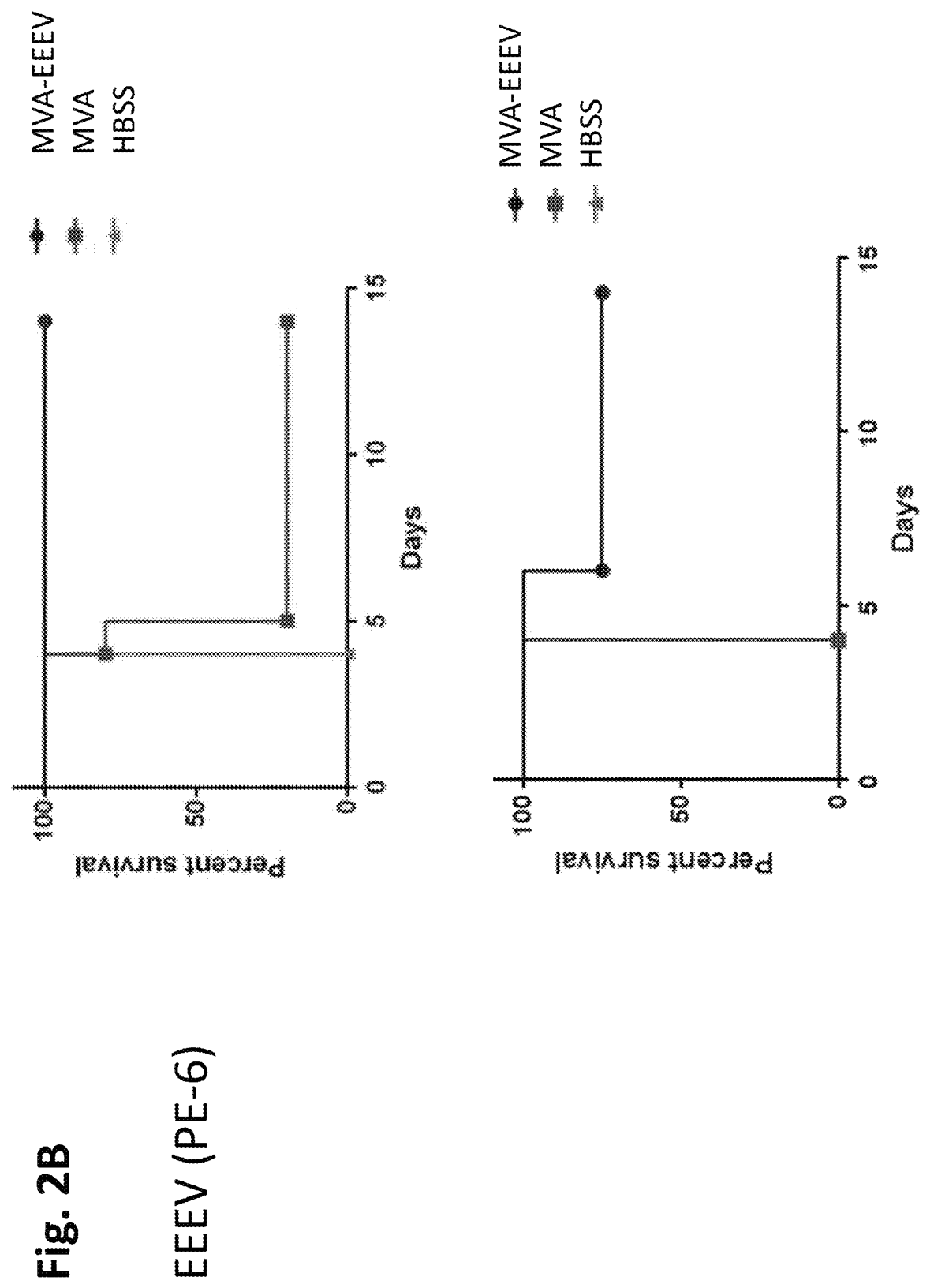

FIGS. 2A, 2B, and 2C show the efficacy of recombinant MVA in a lethal murine challenge model as described in example 5 at low (1,000 pfu) and high dose (10,000 pfu). 5 mice per group received a prime/boost (d0, d28); $1 \times 10^8$ $TCID_{50}$ of MVA-VEEV (MVA-mBN395A), MVA-WEEV (MVA-mBN394A) or MVA-EEEV (MVA-mBN393A); s.c. (WEEV and EEEV), i.m. (VEEV). Challenge was done at day 42 at 1,000 or 10,000 pfu (i.n.), 14 days follow-up. FIG. 2A: Challenge with WEEV (71V-1658), FIG. 2B: Challenge with EEEV (PE-6), FIG. 2C: Challenge with VEEV (TrD). The top diagram shows survival data with 1,000 pfu, the diagram at the bottom shows survival data with 10,000 pfu.

FIGS. 3A and 3B show antigen expression for monovalent and trivalent EEV expression (example 4). FIG. 3A: Surface antigen expression of recombinant MVA containing only a single expression cassette on the surface of transduced HeLa cells according to example 4. EEEV (MVA-mBN393A, GFP), WEEV (MVA-mBN394A, GFP), EEEV (MVA-mBN395A, GFP). Specific expression for each construct respectively is indicated by arrowheads. Control: empty MVA vector and as grey area w/o α-EEV (RFP) FIG. 3B: Surface antigen expression of trivalent MVA (MVA-EEEV/WEEV/VEEV, MVA-mBB396A, GFP/RFP, indicated by arrowheads) compared to monovalent recombinant MVA containing a single expression cassette for EEEV (MVA-mBN393A), WEEV (MVA-mBN394A) or VEEV (MVA-mBN395A) as described in the examples. All vaccines (trivalent and monovalent) contain the surface antigens (E3-E2-6k-E1) of the respective viruses. Control: w/o α-EEV (RFP), grey area.

FIGS. 5A, 5B, and 5C the results of anti-alphavirus neutralizing titers as determined according to example 7 after vaccination with MVA-mBN393A, MVA-mBN394A, MVA-mBN395A or a mixture of the three vaccines (MVA-mBN393A, MVA-mBN394A and MVA-mBN395A) according to the vaccination protocol as described in example 5. The neutralizing titer is defined as the reciprocal of the highest dilution of serum capable of neutralizing 100 $TCID_{50}$ of the respective virus. FIG. 5A: 100 $TCID_{50}$ TrD, MVA-BN-VEEV (MVA-mBN395A), FIG. 5B: Fleming and 71V (71V-1658), MVA-BN-WEEV (MVA-mBN394A), FIG. 5C: PE6, MVA-BN-EEEV (MVA-mBN393A). Control: MVA-BN.

FIG. 6 shows survival rates of animal studies in BALB/c mice vaccinated with MVA-BN-EEEV (MVA-mBN393A), MVA-BN-WEEV (MVA-mBN394A), MVA-BN-VEEV (MVA-mBN395A) or a mixture of the three vaccines (MVA-mBN393A, MVA-mBN394A and MVA-mBN395A) for which the neutralizing titers are shown in FIGS. 5A, 5B, and 5C. Mice received 1×10$^8$ TCID$_{50}$ per dose at day 0 and 28 days except for MVA-BN trivalent (MVA-mBN396A) given at a dose of 3.6×10$^7$ TCID$_{50}$. Challenge was done at 42 days with the virus as indicated.

FIG. 7 shows a summary of survival rates of repeated animal studies in BALB/c mice vaccinated with constructs and doses as described for FIG. 6 according to details given in the examples. ** indicates a heterologous challenge (challenge strain was different compared to the vaccine strain used).

DEFINITIONS

Figure 2C:
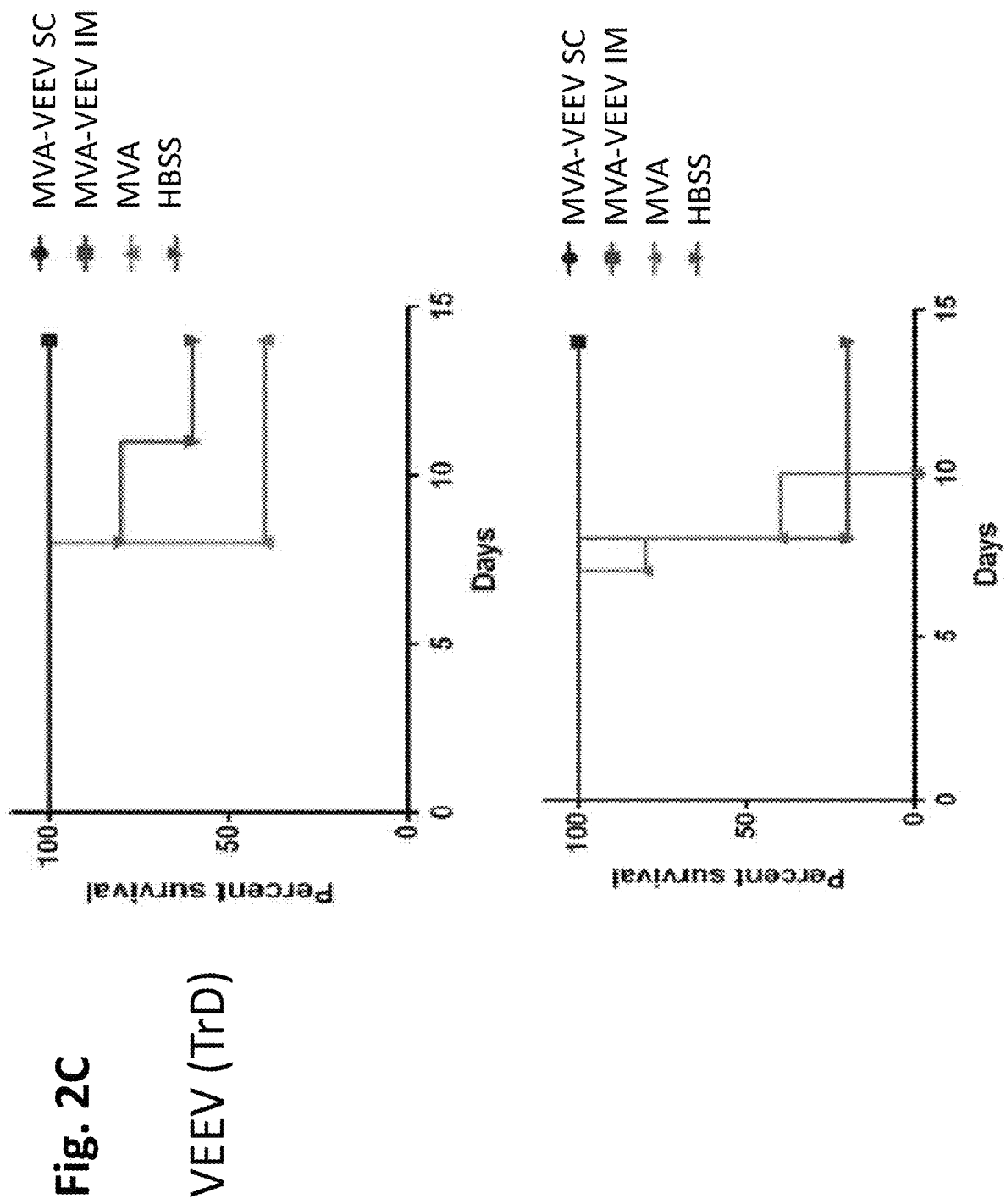

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

It must be noted that, as used herein, the singular forms "a", "an", and "the" include plural references unless the context clearly indicates otherwise. Thus, for example, reference to "a structural protein" includes one or more structural proteins and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "about" when used in connection with a numerical value is meant to encompass numerical values within a range having a lower limit that is 5% smaller than the indicated numerical value and having an upper limit that is 5% larger than the indicated numerical value unless the context clearly indicates otherwise.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having". Any of the aforementioned terms (comprising, containing, including, having), whenever used herein in the context of an aspect or embodiment of the present invention may be substituted with the term "consisting of", though less preferred.

When used herein "consisting of" excludes any element, step, or ingredient not specified in the claim element. When used herein, "consisting essentially of" does not exclude materials or steps that do not materially affect the basic and novel characteristics of the claim.

An "adjuvant" means a vehicle to enhance antigenicity. An adjuvant can include: (1) suspensions of minerals (alum, aluminum hydroxide, and/or phosphate) on which antigen is adsorbed; (2) water-in-oil emulsions in which an antigen solution is emulsified in mineral oil (Freund's incomplete adjuvant), sometimes with the inclusion of killed mycobacteria (Freund's complete adjuvant) to further enhance antigenicity by inhibiting degradation of antigen and/or causing an influx of macrophages; (3) immunostimulatory substances including but not limited oligonucleotides such as, for example, those including a CpG motif can also be used as adjuvants (for example see U.S. Pat. Nos. 6,194,388; and 6,207,646); and (4) purified or recombinant proteins such as costimulatory molecules (e.g., B7-1, ICAM-1, LFA-3, and GM-CSF).

As used herein, "affecting an immune response" includes the development, in a subject, of a humoral and/or a cellular immune response to a protein and/or polypeptide produced by the recombinant MVA and/or compositions and/or vaccines comprising the recombinant MVA of the invention. A "humoral" immune response, as this term is well known in the art, refers to an immune response comprising antibodies, while the "cellular" immune response, as this term is well known in the art, refers to an immune response comprising T-lymphocytes and other white blood cells, especially the immunogen-specific response by HLA-restricted cytolytic T-cells, i.e., "CTLs." A cellular immune response occurs when the processed immunogens, i.e., peptide fragments, are displayed in conjunction with the major histocompatibility complex.

As used herein, the term "alphavirus" has its conventional meaning in the art, and includes the various species of Venezuelan equine encephalitis virus (VEEV), western equine encephalitis virus (WEEV), and eastern equine encephalitis virus (EEEV). "Equine encephalitis virus (EEV)" as used herein includes VEEV, WEEV and EEEV and its strains and isolates.

By "animal" it is intended mammals, birds, and the like. Animal or host includes mammals and human. The animal may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), ovine (e.g., sheep), bovine (e.g., cattle), porcine (e.g., pig), caprine (e.g., goat), avian (e.g., chicken, duck, goose, turkey, quail, pheasant, parrot, finches, hawk, crow, ostrich, emu and cassowary), primate (e.g., prosimian, tarsier, monkey, gibbon, ape), and fish.

The polynucleotides of the disclosure include sequences that are degenerate as a result of the genetic code, e.g., optimized codon usage or codon usage adaptation for expression in a specific host in particular for mammalian expression. As used herein, "optimized" or "optimization" refers to a polynucleotide that is genetically engineered to increase its expression in a given species. To provide optimized polynucleotides coding for EEV polypeptides, the DNA sequence of the EEV protein gene can be modified to 1) comprise codons preferred by highly expressed genes in a particular species; 2) comprise an A+T or G+C content in nucleotide base composition to that substantially found in said species; 3) form an initiation sequence of said species; or 4) eliminate sequences that cause destabilization, inappropriate polyadenylation, degradation and termination of RNA, or that form secondary structure hairpins or RNA splice sites. Increased expression of EEV protein in said species can be achieved by utilizing the distribution frequency of codon usage in eukaryotes and prokaryotes, or in a particular species. The term "frequency of preferred codon usage" refers to the preference exhibited by a specific host cell in usage of nucleotide codons to specify a given amino acid. There are 20 natural amino acids, most of which are specified by more than one codon. Therefore, all degenerate nucleotide sequences are included in the disclosure as long as the amino acid sequence of the EEV polypeptide encoded by the nucleotide sequence is functionally unchanged.

As used herein, a nucleotide sequence having "essentially the same expression level (e.g., transcriptional and/or protein level)" as measured by amount of mRNA (transcription level) and/or recombinant protein (protein level) means at least 75%, 80%, 85%, 90%, 95% or about 100% when compared between the expression of at least two coding sequences of interest e.g., envelope, structural proteins or structural polyproteins of the present invention. As an example the nucleotide sequence of the polyprotein without the capsid protein of VEEV, WEEV and/or EEEV are expressed at essentially the same expression level as determined e.g., after transduction of Vero or HeLa cells with the recombinant MVA or recombinant MVAs of the present invention. Whether or not a sequence in question has "essentially the same expression level" may be readily determined by one ordinary skilled in the art using methods for quantification of mRNA and/or protein e.g., RT-PCR, FACS or western blot or any other method well known to the skilled person. An example of how to determine the expression is given in example 4 of the present invention.

The term "excluding encoding for a capsid protein of the EEV" as used herein can be used interchangeable with "with the proviso that the recombinant MVA does not comprise or contain a nucleotide sequence encoding for a capsid protein of an EEV. The capsid protein of the term also includes any fragment of the capsid protein of the EEV. Thus, neither a full length capsid protein nor a fragment thereof is encoded by the recombinant MVA of the present invention.

As used herein, the terms "expressed", "express", "expression" and the like which can be used interchangeable denote the transcription alone as well as both the transcription and translation of a sequence of interest. Thus, in referring to expression of a nucleotide sequence present in the form of DNA, the product resulting from this expression may be either RNA (resulting from transcription alone of the sequence to be expressed) or a polypeptide sequence (resulting from both transcription and translation of the sequence to be expressed). The term "expression" thus also includes the possibility that both RNA and polypeptide product result from said expression and remain together in the same shared milieu. For example, this is the case when the mRNA persists following its translation into polypeptide product.

As used herein, the term "expression cassette" is defined as a part of a vector or recombinant virus typically used for cloning and/or transformation. An expression cassette is typically comprised of a) one or more coding sequences (e.g., open reading frame (ORF), genes, nucleic acids encoding a protein and/or antigen), and b) sequences controlling expression of one or more coding sequences (e.g., a promoter). Additionally, an expression cassette may comprise a 3' untranslated region (e.g., a transcriptional terminator such as a vaccinia transcriptional terminator). "Expression cassette" can be used interchangeable with the term "transcriptional unit".

"Formulation" refers to a composition containing an active pharmaceutical or biological ingredient e.g., a recombinant MVA of the present invention, along with one or more additional components. The term "formulation" is used interchangeably with the terms "pharmaceutical composition," "vaccine composition," and "vaccine formulation" herein. The formulations can be liquid or solid (e.g., lyophilized).

The term "gene" is used broadly to refer to any segment of polynucleotide associated with a biological function. Thus, genes include introns and exons as in genomic sequence, or just the coding sequences as in cDNAs or viral RNA and/or the regulatory sequences required for their expression. For example, gene also refers to a nucleic acid fragment that expresses mRNA or functional RNA, or encodes a specific protein, and which includes regulatory sequences.

As used herein, a "heterologous" gene, nucleic acid, antigen, or protein is understood to be a nucleic acid or amino acid sequence which is not present in the wild-type poxviral genome (e.g., MVA or MVA-BN). The skilled person understands that a "heterologous gene", when present in a poxvirus such as MVA or MVA-BN, is to be incorporated into the poxviral genome in such a way that, following administration of the recombinant poxvirus to a host cell, it is expressed as the corresponding heterologous gene product, i.e., as the "heterologous antigen" and/or "heterologous protein." Expression is normally achieved by operatively linking the heterologous gene to regulatory elements that allow expression in the poxvirus-infected cell. Preferably, the regulatory elements include a natural or synthetic poxvirus promoter.

The term "immunogenic composition" or "immunological composition" covers a composition that elicits an immune response against an antigen of interest expressed from the MVA. The term "vaccine or vaccine composition" covers any composition that induces a protective immune response against the antigens of interest, or which efficaciously protects against the antigen of interest; e.g., after administration or injection into the animal or human elicits a protective immune response against the antigen or provides efficacious protection against the antigen expressed from the MVA vector. The composition can be administered alone, or can be administered sequentially with other compositions or therapeutic compositions thereby providing a combination composition, a cocktail or multivalent mixture of two or more preferably three, four, five or six compositions.

The term "nucleic acid", "nucleotide sequence", "nucleic acid sequence" and "polynucleotide" can be used interchangeable and refers to RNA or DNA that is linear or branched, single or double stranded, or a hybrid thereof. The term also encompasses RNA/DNA hybrids. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism.

The term "open reading frame" (ORF) refers to a sequence of nucleotides, that can be translated into amino acids. Typically, such an ORF contains a start codon, a subsequent region usually having a length which is a multiple of 3 nucleotides, but does not contain a stop codon (TAG, TAA, TGA, UAG, UAA, or UGA) in the given reading frame. Typically, ORFs occur naturally or are constructed artificially, i.e., by gene-technological means. An ORF codes for a protein where the amino acids into which it can be translated form a peptide-linked chain. As used herein, the term "essential ORF" means an ORF which when being experimentally partially or fully deleted e.g., in MVA, the MVA virus replication, growth or both replication and growth are reduced (e.g., by at least 15 fold in the mutant compared to the MVA without deletion). Methods to determine MVA virus replication and growth of the virus are well known to the skilled person. For example methods are described in Vaccinia Virus and Poxvirology, Methods and Protocols, Volume 269 Ed. By Stuart N. Isaacs (Humana Press (2004), see e.g., Chapter 8, Growing Poxviruses and determining Virus Titer, Kotwal and Abrahams). Viral growth rates of MVA may be determined by GFP fluorescence as for example described in Orubu et al. (2012) PLOS One 7:e40167 using e.g., CEF cells or the method as described in Hornemann et al. (2003), Journal of Virology 77:8394-8407.

As used herein, "operably linked" means that the components described are in relationship permitting them to function in their intended manner e.g., a promoter to transcribe the nucleic acid to be expressed. A first nucleic acid sequence is operably linked to a second nucleic acid sequence when the first nucleic acid sequence is placed in a functional relationship with the second nucleic acid sequence. For example, a promoter is operably linked to a coding sequence if the promoter is placed in a position where it can direct transcription of the coding sequence. Generally, operably linked DNA sequences are contiguous and, where necessary to join two protein-coding regions, in the same reading frame.

"Percent (%) sequence homology or identity" with respect to nucleic acid sequences described herein is defined as the percentage of nucleotides in a candidate sequence that are identical with the nucleotides in the reference sequence (i.e., the nucleic acid sequence from which it is derived), after aligning the sequences and introducing gaps, if necessary, to achieve the maximum percent sequence identity, and not considering any conservative substitutions as part of the sequence identity. Alignment for purposes of determining percent nucleotide sequence identity or homology can be achieved in various ways that are within the skill in the art, for example, using publically available computer software such as BLAST, ALIGN, or Megalign (DNASTAR) software. Those skilled in the art can determine appropriate parameters for measuring alignment, including any algorithms needed to achieve maximum alignment over the full length of the sequences being compared. For example, an appropriate alignment for nucleic acid sequences is provided by the local homology algorithm of Smith and Waterman, (1981), Advances in Applied Mathematics 2:482-489. This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov (1986), Nucl. Acids Res. 14(6):6745-6763. An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." The same applies to "percent (%) amino acid identity", mutatis mutandis. Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://http://blast.ncbi.nlm.nih.gov/.

The terms "pharmaceutical", "pharmaceutical composition" and "medicament" are used interchangeably herein referring to a substance and/or a combination of substances being used for the prevention or treatment of a disease.

"Pharmaceutically acceptable" means that the carrier or excipient, at the dosages and concentrations employed, will not cause any unwanted or harmful effect(s) in the subject(s) to which they are administered.

"Pharmaceutically acceptable carriers" are for example described in Remington's Pharmaceutical Sciences, by E. W. Martin, Mack Publishing Co., Easton, Pa., 15th Edition (1975); Remington's Pharmaceutical Sciences, 18th edition, A. R. Gennaro, Ed., Mack Publishing Company (1990); Pharmaceutical Formulation Development of Peptides and Proteins, S. Frokjaer and L. Hovgaard, Eds., Taylor & Francis [2000]; and Handbook of Pharmaceutical Excipients, 3rd edition, A. Kibbe, Ed., Pharmaceutical Press (2000). They describe compositions and formulations using conventional pharmaceutically acceptable carriers suitable for administration of the vectors and compositions disclosed herein. Generally the nature of the carrier used depends on the particular mode of administration being employed. For example, parenteral formulations usually comprise injectable fluids that include pharmaceutically and physiologically acceptable fluids such as water, physiological saline, balanced salt solutions, aqueous dextrose, glycerol or the like, as a vehicle. For solid compositions (such as powders, pills, tablets, or capsules), conventional non-toxic solid carriers include, for example, pharmaceutical grades of mannitol, lactose, starch, or magnesium stearate. Pharmaceutical compositions can also contain minor amounts of non-toxic auxiliary substances such as wetting or emulsifying agents, preservatives, pH-buffering agents and the like such as, for example, sodium acetate or sorbitan monolaurate.

As used herein, "prevent", "preventing", "prevention", or "prophylaxis" of a disease or infection means preventing that such disease occurs in subject (e.g., human or animal).

The term "prime-boost vaccination" refers to a vaccination strategy using a first, priming injection of a vaccine targeting a specific antigen followed at intervals by one or more boosting injections of the same vaccine. Prime-boost vaccination may be homologous or heterologous. A homologous prime-boost vaccination uses a vaccine comprising the same immunogen and vector for both the priming injection and the one or more boosting injections. A heterologous prime-boost vaccination uses a vaccine comprising the same immunogen for both the priming injection and the one or more boosting injections but different vectors for the priming injection and the one or more boosting injections. For example, a homologous prime-boost vaccination may use a recombinant MVA vector comprising the same nucleic acids expressing alphavirus antigens for both the priming injection and the one or more boosting injections. In contrast, a heterologous prime-boost vaccination may use a recombinant MVA vector comprising nucleic acids expressing one alphavirus protein for the priming injection and another recombinant MVA vector expressing a second one alphavirus protein not contained in the priming injection or vice versa. Heterologous prime-boost vaccination also encompasses various combinations such as, for example, use of a plasmid encoding an immunogen in the priming injection and use of a recombinant MVA encoding the same immunogen in the one or more boosting injections, or use of a recombinant protein immunogen in the priming injection and use of a recombinant MVA vector encoding the same protein immunogen in the one or more boosting injections.

As used herein, the term "promoter" denotes a regulatory region of nucleic acid, usually DNA, located upstream of the sequence of a nucleic acid to be expressed, which contains specific DNA sequence elements, that are recognized and bound e.g., by protein transcription factors and polymerases responsible for synthesizing the RNA from the coding region of the gene being promoted. As promoters are typically immediately adjacent to the gene in question, positions in the promoter are designated relative to the transcriptional start site, where transcription of DNA begins for a particular gene (i.e., positions upstream are negative numbers counting back from −1, for example −100 is a position 100 base pairs upstream). Thus, the promoter sequence may comprise nucleotides until position −1. However, nucleotides from position +1 are not part of the promoter, i.e., in this regard it has to be noted that the translation initiation codon (ATG or AUG) is not part of the promoter. Thus, SEQ ID NOs: 7 or 8 are polynucleotides comprising promoters of the invention. A "natural poxvirus promoter" as used herein means an endogenous promoter of the poxvirus genome. A "synthetic poxvirus promoter" means a recombinant engineered promoter active to direct transcription of the nucleic acid to be expressed by a poxvirus (e.g., MVA in CEF cells). The term "26S promoter" is well known to the skilled person and refers to a subgenomic promoter of a 26S RNA of an alphavirus which is usually contained in a single open reading frame (e.g., of capsid-E3-E2-6K-E1 of VEEV). The mRNA encoding the structural proteins of EEVs e.g., VEEV is usually transcribed from a replication intermediate and a 26S subgenomic RNA promoter.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

The term "recombinant" when applied to a nucleic acid, vector, e.g., MVA and the like refers to a nucleic acid, vector, or made by an artificial combination of two or more otherwise heterologous segments of nucleic acid sequence, or to a nucleic acid, vector or comprising such an artificial combination of two or more otherwise heterologous segments of nucleic acid sequence. The artificial combination is most commonly accomplished by artificial manipulation of isolated segments of nucleic acids, using well-established genetic engineering techniques. Generally, a "recombinant" MVA as described herein refers to MVAs that are produced by standard genetic engineering methods, i.e., MVAs of the present invention are thus genetically engineered or genetically modified MVAs. The term "recombinant MVA" thus includes MVAs (e.g., MVA-BN) which have stably integrated recombinant nucleic acid, preferably in the form of a transcriptional unit, in their genome. A transcriptional unit may include a promoter, enhancer, terminator and/or silencer. Recombinant MVAs of the present invention may express heterologous antigenic determinants, polypeptides or proteins (antigens) upon induction of the regulatory elements.

As used herein, the term "protective immunity" or "protective immune response" means that the vaccinated subject is able to control an infection with the pathogenic agent against which the vaccination was done. Usually, the subject having developed a "protective immune response" develops only mild to moderate clinical symptoms or no symptoms at all. In cases where the infection would be expected lethal without countermeasures, a subject having a "protective immune response" or "protective immunity" against a certain agent will not die as a result of the infection with said agent.

The term "reference sample" as used herein, refers to a sample which is analyzed in a substantially identical manner as the sample of interest and whose information is compared to that of the sample of interest. A reference sample thereby provides a standard allowing for the evaluation of the information obtained from the sample of interest. A reference sample may be identical to the sample of interest except for one component which may be exchanged, missing or added.

As used herein, "solely E3, E2, 6k and E1" refers to structural proteins or a structural polyprotein not comprising the capsid protein. In one non-limiting example, solely E3, E2, 6k and E1 may be the structural proteins E3, E2, 6K and E1 of an equine encephalitis virus e.g., of FL93-939 or EEEV V105-00210 excluding further structural protein(s) of the same virus or any other equine encephalitis virus.

The term "structural protein" of an EEV refers to a structural protein/polyprotein encoded by the RNA of an EEV (e.g., any of the WEEVs, VEEVs or EEEVs as described herein). The structural protein is usually produced by the virus as a structural polyprotein of five proteins i.e., C, E3, E2, 6k and E1 and is represented generally in the literature as C-E3-E2-6k-E1. E3 and 6k are also described as membrane translocation/transport signals for the two glycoproteins, E2 and E1. Nucleotide sequences encoding "structural proteins" as used herein means a nucleotide sequence encoding proteins which are required for encapsidation (e.g., packaging) of the viral genome, and include the capsid protein, E1 glycoprotein, and E2 glycoprotein. "Structural polyprotein" of EEV refers to the polyprotein C-E3-E2-6k-E1 of an EEV.

A "subject" means a living multi-cellular vertebrate organisms, including, for example, humans, non-human mammals and birds. The term "subject" may be used interchangeably with the term "animal" herein.

The term "transcription level" or "protein level" related to a specific promoter as used herein refers to the amount of gene/nucleic acid product present in the body or a sample at a certain point of time. The transcription or protein level (e.g., transcription of nucleic acid as mRNA or protein amount translated form the mRNA) can for example be determined, measured or quantified by means of the mRNA or protein expressed from the gene/polynucleotide e.g., as encoded by the recombinant MVA of the present invention. Gene expression can result in production of the protein, by transcription of the gene by RNA polymerase to produce a messenger RNA (mRNA) that contains the same protein-encoding information and translation of the mRNA by ribosomes to produce the protein. The term "transcribed" or "transcription" refers to the process of copying a DNA sequence of the gene by RNA polymerase into the mRNA, using the DNA as a template. The term "translated" or "translation" refers to the process by which the information contained in the mRNA is used as a blueprint to synthesize the protein. The transcription or protein level can for example be quantified by normalizing the amount mRNA or of protein of interest present in a sample with the total amount of gene product of the same category (mRNA or total protein) in the same sample or a reference sample (e.g., taken at the same time from the same sample). The transcription can be measured or detected by means of any method as known in the art, e.g., methods for the indirect detection and measurement of the gene product of interest that usually work via binding of the gene product of interest with one or more different molecules or detection means (e.g., primer(s), probes, antibodies, protein scaffolds) specific for the gene product of interest. Such methods include for example RT-PCR and/or quantitative PCR. The determination of the level of protein can be measured or detected by means of any known method as known to the artisan, e.g., western blot, ELISA, or mass spectrometry.

As used herein, "transcriptional terminator" is comprised of a DNA sequences involved in specific termination of an RNA transcript by an RNA polymerase. Vaccinia virus including MVA RNA polymerase terminates transcription downstream of an RNA signal (UUUUUNU, TTTTTNT or T5NT on the DNA level) in the nascent RNA (Earl et al. (1990), J. Virol. 64:2448-2451). "Transcriptional terminator" is sometimes referred to as a "termination signal" in the literature and thus can be used interchangeable.

As used herein, "treat", "treating" or "treatment" of a disease means the prevention, reduction, amelioration, partial or complete alleviation, or cure of a disease e.g., an EEV-caused disease. It can be one or more of reducing the severity of the disease, limiting or preventing development of symptoms characteristic of the disease being treated, inhibiting worsening of symptoms characteristic of the disease being treated, limiting or preventing recurrence of the disease in a subject who has previously had the disease, and limiting or preventing recurrence of symptoms in subjects.

As used herein, "trivalent" in combination with vaccine or recombinant MVA means that the vaccine or recombinant MVA has a valence against three different viruses and generates a protective immune response against antigens (e.g., structural proteins or structural polyproteins) of those different viruses. Thus, in the context of a trivalent MVA vaccine of the invention trivalent means a valence against three different viruses of which antigens are encoded by the MVA vaccine or vaccine comprising a recombinant MVA expressing the nucleic acids encoding for the antigens e.g., structural proteins or structural polyproteins of VEEV, WEEV and EEEV. Another example for trivalent which is also covered by the meaning of trivalent is that the three different viruses are different virus strains e.g., two WEEV strains such as for example 71V-1658 and Fleming in addition to a VEEV or EEEV strain. In the latter case the recombinant MVA of the present invention for example comprises a nucleotide sequence encoding for the proteins (e.g., structural protein, structural polyprotein, envelope protein) of WEEV 71V-1658, WEEV Fleming and of an EEEV strain e.g., EEEV V105-00210. In comparison "monovalent" means that the vaccine or recombinant MVA has a valence against only one virus of a particular species, such as only VEEV, only WEEV or only EEEV and generates a protective immune response against only one structural protein or structural polyprotein of one virus. It does not exclude however the generation of protective immune responses against several closely related virus subtypes. "Divalent" thus means that the vaccine or recombinant MVA has a valence against two viruses.

A "vector" refers to a recombinant DNA or RNA plasmid or virus that comprises a heterologous polynucleotide to be delivered to a target cell, either in vitro or in vivo. The heterologous polynucleotide may comprise a sequence of interest for purposes of prevention or therapy, and may optionally be in the form of an expression cassette. As used herein, a vector needs not be capable of replication in the ultimate target cell or subject. The term includes cloning vectors and viral vectors.

The term "viral replicon" as used in the context of the present invention is used to refer to RNA or DNA comprising portions of the 49S viral genomic RNA that are essential for transcription and for cytoplasmic amplification of the transported RNA and for subgenomic RNA expression of a heterologous nucleic acid sequence. Thus, the replicon encodes and expresses viral non-structural proteins necessary for cytoplasmic amplification of the virus RNA.

In the context of the present invention the term "virus" or "recombinant virus" refers to an infectious or non-infectious virus comprising a viral genome. In this case the nucleic acids, promoters, recombinant proteins, and/or expression cassettes as mentioned herein are part of the viral genome of the respective recombinant virus. The recombinant viral genome is packaged and the obtained recombinant viruses can be used for the infection of cells and cell lines, in particular for the infection of living animals including humans.

Several documents are cited throughout the text of this specification. Each of the documents cited herein (including all patents, patent applications, scientific publications, manufacturer's specifications, instructions, etc.), whether supra or infra, are hereby incorporated by reference in their entirety. To the extent the material incorporated by reference contradicts or is inconsistent with this specification, the specification will supersede any such material. Nothing herein is to be construed as an admission that the invention is not entitled to antedate such disclosure by virtue of prior invention.

DETAILED DESCRIPTION OF THE INVENTION

Reference will now be made in detail to exemplary embodiments of the invention, examples of which are illustrated in the accompanying drawings.

In one aspect, the present invention provides a recombinant modified vaccinia virus Ankara (MVA) comprising a nucleotide sequence of a poxvirus promoter operably linked to a nucleotide sequence encoding for a structural protein, preferably a structural polyprotein, of an equine encephalitis virus (EEV) excluding encoding for a capsid protein of the EEV.

In particular embodiments of the invention, the EEV is selected from the group of western equine encephalitis virus (WEEV), Venezuelan equine encephalitis (VEEV) and/or eastern equine encephalitis virus (EEEV).

As shown herein for the first time, a recombinant MVA comprising a nucleotide sequence of a poxvirus promoter operably linked to a nucleotide sequence encoding for a structural polyprotein of the equine encephalitis virus (EEV) excluding encoding for a capsid protein of the EEV provides a vaccine that protects against WEEV, VEEV and/or EEEV in subjects. This was surprising as the prior art using vaccinia virus based vectors encoding for structural proteins of VEEV were unable to protect against airborne challenge and fail to offer full protection against respiratory VEEV exposure even when vaccinated with E3-E2-6k-E1 recombinant vaccinia virus (Phillpotts et al. (2000) as cited above). It is the first report showing that recombinant poxvirus such as MVA can induce a protective immune response in mice in a WEEV and EEEV challenge study. Similar efficacy and immunogenicity results could be achieved for the three alphaviruses although there are differences between them. WEEV and EEEV are neurotropic viruses that produce limited viremia wherein VEEV produces a systemic febrile disease (Nagata et al. (2013), Future Virol. 8:661-674). In contrast to VEEV, EEEV poorly replicates in lymphocytes and fails to replicate in dendritic cells and macrophages. It could also be demonstrated that a combined application of recombinant MVA comprising nucleotide sequences encoding antigens against WEEV, VEEV, and EEEV offers protection against challenge with all three alphaviruses by respiratory challenge in mice. An additional advantage is that the recombinant MVA can be administered via a mucosa route eliciting a protection against aerosol challenge.

In particular embodiments, the nucleotide sequence encoding for the structural protein or structural polyprotein is derived from one or more western equine encephalitis virus (WEEV), preferably further comprising a nucleotide sequence encoding for a second or third structural protein or structural polyprotein of an EEV selected from the group consisting of Venezuelan (VEEV) and/or eastern equine encephalitis virus (EEEV).

In particular embodiments, the nucleotide sequence encoding for the structural polyprotein is derived from one or more Venezuelan equine encephalitis virus (VEEV), preferably further comprising a nucleotide sequence encoding for a second or third structural protein or structural polyprotein of an EEV selected from the group consisting of western (WEEV) and/or eastern equine encephalitis virus (EEEV).

In particular embodiments, the nucleotide sequence encoding for the structural polyprotein is derived from one or more eastern equine encephalitis virus (EEEV), preferably further comprising a nucleotide sequence encoding for a second or third structural protein or structural polyprotein of an EEV selected from the group consisting of Venezuelan (VEEV) and/or western equine encephalitis virus (WEEV).

In particular embodiments, the recombinant MVA comprises one, two, or three nucleotide sequences each comprising a poxvirus promoter operably linked to a nucleotide sequence encoding for any structural protein or any structural polyprotein of the EEV as described herein excluding encoding for a capsid protein of the EEV. Preferably, none of the nucleotide sequences encoding for the structural proteins or structural polyproteins as described herein encode for a capsid protein of the EEV.

Sequences of EEVs such as Venezuelan (VEEV), eastern (EEEV), and western equine encephalitis viruses (WEEV) and strains thereof (e.g., Trinidad Donkey, Fleming), as well as the proteins encoded thereby (e.g., E3, E2, 6k, E1), are available to the skilled person in public databases, such as the GenBank sequence database provided by the National Center for Biotechnology Information (NCBI).

EEV Viruses, Proteins and Nucleotide Sequences

EEV are alphavirus belonging to the family of Togaviridae. EEV are small, enveloped positive-strand RNA viruses well known in the art. The viral nucleocapsid is surrounded by host derived lipid membranes in which a trimer of envelope proteins of E1 and E2 heterodimers are embedded. The nucleocapsid consists of a capsid protein (C) surrounded the single-strand RNA genome. The RNA genome (49S RNA) of EEV viruses is approximately 11-12 kb in length and contains a 5' cap and 3' polyadenylation tail and is immediately translated upon entry into the cell. The 5' region of the genome encodes for four non-structural proteins (NSP1, NSP2, NSP3, and NSP4). The 3' region of the genome encodes for five structural proteins (C, E3, E2, 6k, E1) which are expressed as a structural polyprotein from 26S subgenomic RNA. The mRNA encoding for the structural proteins is transcribed from a replication intermediate and a 26S subgenomic promoter. Protease cleavage of the polyprotein produces the mature structural proteins C, E3, E2, 6k, E1. The nucleocapsid (C) protein possesses autoproteolytic activity which cleaves the C protein from the precursor protein soon after the ribosome transits the junction between the C and E3 protein coding sequence. Subsequently, the envelope glycoproteins E2 and E1 are derived by proteolytic cleavage and form heterodimers. E2 initially appears in the infected cell as a precursor, pE2, which consists of E3 and E2. After glycosylation and transit through the endoplasmic reticulum and the Golgi apparatus, E3 is cleaved from E2 by furin-like protease activity at a cleavage site.

In certain embodiments of the invention, the structural protein or structural polyprotein comprises or consists of less than 5 structural proteins, preferably 4 structural proteins.

In certain embodiments of the invention, the structural protein or structural polyprotein comprises E2 and E1.

In certain embodiments of the invention, the structural protein(s) or structural polyprotein solely comprises or consists of E3, E2, 6k and E1.

Various strains and subtypes of EEVs such as Venezuelan (VEEV), eastern (EEEV), and western equine encephalitis viruses (WEEV) are known to the skilled person and are encompassed by the embodiments of the invention. In particular embodiments of the present invention, the WEEV may be one or more (e.g., one, two, three or four) of the WEEV strains or isolates selected from the group of WEEV Fleming, McMillan, 71V-1658, CBA87, California, Mn520, Mn548 and B-11, preferably WEEV Fleming, 71V-1658 and CBA87. WEEVs are e.g., described in Nagata et al. (2006), Journal of General Virology 87:2353-61. Thus, in a preferred embodiment, the WEEV may be one or more (e.g., one, two, three or four) of the WEEV strains selected from the group of WEEV Fleming, McMillan, 71V-1658, CBA87, California, Mn520, Mn548 and B-11, preferably selected from the group of WEEV Fleming, 71V-1658 and CBA87, most preferably WEEV 71V-1658.

In particular embodiments of the present invention, the VEEV is one or more (e.g., one, two, three or four) selected from the group of subtype IAB, IC, IE, IF, Everglades, Mucambo, Pixuna, Cabassou and Rio Negro. Everglades, Mucambo, Pixuna, Cabassou and Rio Negro have previously been described as subtype II to VI, i.e. Everglades (formerly II), Mucambo (formerly III), Pixuna (formerly IV), Cabassou (formerly V), and Rio Negro (formerly VI) (King et al. (2012), Virus Taxonomy: Classification and Nomenclature of Viruses: Ninth Report of the International Committee on Taxonomy of Viruses. Eds., King A M G, et al. San Diego, Calif., Elsevier Academic Press). Preferably, the VEEV of any of the embodiments herein is one or two VEEV selected from the group of subtype IAB and IC.

In particular embodiments, the VEEV of any of the embodiments herein may be one or more (e.g., two or three) of the VEEV strains or isolates selected from the group of VEEV Trinidad Donkey (TrD), INH-9813, and INH-6803, preferably selected from the group of VEEV Trinidad Donkey (TrD) and INH-9813, most preferably VEEV Trinidad Donkey (TrD).

In particular embodiments, the EEEV of any of the embodiments herein is a North American and Caribbean (NA EEEV) and/or South American (SA EEEV) EEEV. The South American (SA EEEV) has been re-classified as Madariaga virus (MADV II-IV) as described in King et al. (King et al. (2012), Virus Taxonomy: Classification and Nomenclature of Viruses: Ninth Report of the International Committee on Taxonomy of Viruses. Eds., King A M G, et al. San Diego, Calif., Elsevier Academic Press).

In yet other embodiments, the EEEV of any of the embodiments herein may be one or more (e.g., one, two, three or four) of the EEEV strains or isolates selected from the group of EEEV New Jersey 60, NJ 1959, 82V-2137, FL93-939, FL-91-4679, PE6, and V105-00210, preferably selected from the group of FL93-939, FL-91-4679, PE6, and V105-00210, more preferably one or more (e.g., one, two, three or four) selected from the group of FL93-939, PE6, and V105-00210, further preferably EEEV V105-00210.

In certain embodiments, the nucleotide sequence encoding for a structural protein or structural polyprotein of the WEEV, VEEV and/or EEEV is selected from strain CBA87, 71V-1658, FL93-939, Fleming, TrD, INH-9813, INH-6803, 71V-1658, PE-6, FL91-4679, and/or V105-00210, preferably FL93-939, TrD, Fleming and/or V105-00210.

In certain embodiments, the nucleotide sequence encoding for a structural protein or structural polyprotein of the WEEV, VEEV and/or EEEV is selected from strain CBA87, 71V-1658, FL93-939, and/or Fleming.

In certain embodiments, the nucleotide sequence encoding for a structural protein or structural polyprotein of the WEEV, VEEV and/or EEEV encodes for the amino acid of the structural protein or structural polyprotein selected from strain CBA87, 71V-1658, FL93-939, Fleming, TrD, INH-9813, INH-6803, 71V-1658, PE-6, FL91-4679, and/or V105-00210, preferably FL93-939, TrD, Fleming and/or V105-00210, preferably excluding encoding for a capsid protein of the virus.

In certain embodiments, the nucleotide sequence encoding for a structural protein or structural polyprotein of the WEEV, VEEV and/or EEEV encodes for the amino acid of the structural protein or structural polyprotein selected from strain CBA87, 71V-1658, FL93-939, and/or Fleming, preferably excluding encoding for a capsid protein of the virus.

It is to be understood that also any combination of any WEEV, EEEV and/or VEEV as mentioned above is also encompassed with any of the embodiments as described herein.

The nucleotide sequence(s) encoding for a structural protein or structural polyprotein of an EEV as mentioned herein refer to nucleotide sequences (e.g., genomic sequences or genes), encoding the corresponding protein in any EEV strain or isolate, even though the exact sequence and/or genomic location of the gene may differ between the strains or isolates. Likewise, the EEV structural proteins or structural polyproteins mentioned herein refer to proteins or variants thereof, encoded and expressed by the corresponding genomic nucleotide sequence. By way of example, the structural protein or structural polyprotein of WEEV comprises an open reading frame spanning nucleotides 7497-11207 (endpoints included) as numbered in GenBank Accession No. GQ287645.1. A nucleotide sequence of the structural protein or structural polyprotein of said WEEV excluding encoding for the capsid protein is set forth in SEQ ID NO:4 starting at position 3 of SEQ ID NO:4. Position 1 to 3 of SEQ ID NO:4 encodes for a methionine. The corresponding amino acid sequence is set forth in SEQ ID NO:1.

An exemplary VEEV structural polyprotein is provided in Genbank Accession No. LO1442.2. A structural polyprotein of WEEV comprises an open reading frame spanning nucleotides 7562-11329 (endpoints included) as numbered in GenBank Accession No. LO1442.2. The nucleotide sequence of the structural protein or structural polyprotein of said VEEV excluding encoding for the capsid protein is set forth in SEQ ID NO:5 starting at position 3 of SEQ ID NO:5. Position 1 to 3 of SEQ ID NO:5 encodes for a methionine. The corresponding amino acid sequence is set forth in SEQ ID NO:2.

An exemplary EEEV structural polypeptide is provided in Genbank Accession No. EF151502.1. A structural polyprotein of EEEV comprise an open reading frame spanning nucleotides 7595-11323 (endpoints included) as numbered in GenBank Accession No. EF151502.1. The nucleotide sequence of the structural protein or structural polyprotein of said EEEV excluding encoding for the capsid protein is set forth in SEQ ID NO:6 starting at position 3 of SEQ ID NO:6. Position 1 to 3 of SEQ ID NO:3 encodes for a methionine. The corresponding amino acid sequence is set forth in SEQ ID NO:3.

In particular embodiments, the nucleotide sequence encoding for a structural protein or structural polyprotein of an EEV excluding encoding for a capsid protein of the EEV encodes for an amino acid sequence which comprises or consists of SEQ ID NO: 1, 2 and/or 3 or a variant thereof.

In particular embodiments, said variant has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity with the referenced protein or polypeptide at the level of the amino acid sequence e.g., the amino acid sequence of SEQ ID NO 1, 2 or 3.

In further particular embodiments, the nucleotide sequence encoding for a structural protein or structural polyprotein of an EEV excluding encoding for a capsid protein of the EEV comprises or consist of SEQ ID NO: 4, 5, and/or 6 or a variant thereof.

In particular embodiments, said variant has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% nucleotide sequence identity with the referenced nucleotide sequence e.g., the nucleotide sequence of SEQ ID NOs 4, 5, and/or 6, preferably wherein the variant does not change the amino acid sequence encoded by the nucleotide sequence of SEQ ID NO: 4, 5 and/or 6.

Modified Vaccinia Virus Ankara (MVA)

Modified vaccinia virus Ankara (MVA) has been generated by more than 570 serial passages on chicken embryo fibroblasts of the dermal vaccinia strain Ankara (Chorioallantois vaccinia virus Ankara virus, CVA; for review see Mayr et al. (1975), Infection 3:6-14) that was maintained in the Vaccination Institute, Ankara, Turkey for many years and used as the basis for vaccination of humans. However, due to the often severe post-vaccination complications associated with vaccinia viruses, there were several attempts to generate a more attenuated, safer smallpox vaccine.

During the period of 1960 to 1974, Prof. Anton Mayr succeeded in attenuating CVA by over 570 continuous passages in CEF cells (Mayr et al. (1975)). It was shown in a variety of animal models that the resulting MVA was avirulent (Mayr, A. & Danner, K. (1978), Dev. Biol. Stand. 41:225-234). As part of the early development of MVA as a pre-smallpox vaccine, there were clinical trials using MVA-517 in combination with Lister Elstree (Stickl (1974), Prev. Med. 3:97-101; Stickl and Hochstein-Mintzel (1971), Munch. Med. Wochenschr. 113: 1149-1153) in subjects at risk for adverse reactions from vaccinia. In 1976, MVA derived from MVA-571 seed stock (corresponding to the 571$^{st}$ passage) was registered in Germany as the primer vaccine in a two-stage parenteral smallpox vaccination program. Subsequently, MVA-572 was used in approximately 120,000 Caucasian individuals, the majority children between 1 and 3 years of age, with no reported severe side effects, even though many of the subjects were among the population with high risk of complications associated with vaccinia (Mayr et al. (1978), Zentralbl. Bacteriol. (B) 167: 375-390). MVA-572 was deposited at the European Collection of Animal Cell Cultures as ECACC V94012707.

As a result of the passaging used to attenuate MVA, there are a number of different strains or isolates, depending on the number of passages conducted in CEF cells. For example, MVA-572 was used in a small dose as a pre-vaccine in Germany during the smallpox eradication program, and MVA-575 was extensively used as a veterinary vaccine. MVA as well as MVA-BN lacks approximately 15% (31 kb from six regions) of the genome compared with ancestral CVA virus. The deletions affect a number of virulence and host range genes, as well as the gene for Type A inclusion bodies.

Even though Mayr et al. demonstrated during the 1970s that MVA is highly attenuated and avirulent in humans and mammals, certain investigators have reported that MVA is not fully attenuated in mammalian and human cell lines since residual replication might occur in these cells (Blanchard et al. (1998), J. Gen. Virol. 79:1159-1167; Carroll & Moss (1997), Virology 238:198-211; U.S. Pat. No. 5,185,146; Ambrosini et al. (1999), J. Neurosci. Res. 55:569). It is assumed that the results reported in these publications have been obtained with various known strains of MVA, since the viruses used essentially differ in their properties, particularly in their growth behaviour in various cell lines. Such residual replication is undesirable for various reasons, including safety concerns in connection with use in humans.

One strain of MVA having enhanced safety profiles for the development of vaccines or pharmaceuticals, has been developed by Bavarian Nordic: MVA was further passaged by Bavarian Nordic and is designated MVA-BN deposited on Aug. 30, 2000 at the European Collection of Cell Cultures (ECACC) under number V00083008.

MVA-BN can attach to and enter human cells where virally-encoded genes are expressed very efficiently. MVA-BN is strongly adapted to primary chicken embryo fibroblast (CEF) cells and does not replicate in human cells. In human cells, viral genes are expressed, and no infectious virus is produced. Preparations of MVA-BN and derivatives have been administered to many types of animals, and to more than 2000 human subjects, including immune-deficient individuals. All vaccinations have proven to be generally safe and well tolerated. Despite its high attenuation and reduced virulence in preclinical studies MVA-BN has been shown to elicit both humoral and cellular immune responses to vaccinia and to heterologous gene products encoded by genes cloned into the MVA genome (E. Harrer et al. (2005), Antivir. Ther. 10:285-300; A. Cosma et al. (2003), Vaccine 22:21-9; M. Di Nicola et al. (2003), Hum. Gene Ther. 14:1347-1360; M. Di Nicola et al. (2004), Clin. Cancer Res., 10:5381-5390).

Although MVA-BN is preferred for its higher safety (less replication competent), all MVAs and those specifically as described herein are suitable for any of the embodiments of the present invention.

Examples of MVA virus strains that are useful in the practice of the present invention and that have been deposited in compliance with the requirements of the Budapest Treaty are strains MVA 572, deposited at the European Collection of Animal Cell Cultures (ECACC), Vaccine Research and Production Laboratory, Public Health Laboratory Service, Centre for Applied Microbiology and Research, Porton Down, Salisbury, Wiltshire SP4 0JG, United Kingdom, with the deposition number ECACC 94012707 on Jan. 27, 1994, and MVA 575, deposited under ECACC 00120707 on Dec. 7, 2000, MVA-BN, deposited on Aug. 30, 2000 at the European Collection of Cell Cultures (ECACC) under number V00083008, and its derivatives, are additional exemplary strains.

"Derivatives" or "variants" of MVA or MVA-BN refer to viruses exhibiting essentially the same replication characteristics as MVA as described herein, but exhibiting differences in one or more parts of their genomes. MVA-BN as well as a derivative or variant of MVA-BN fails to reproductively replicate in vivo in humans and mice, even in severely immune suppressed mice. More specifically, MVA-BN or a derivative or variant of MVA-BN has preferably also the capability of reproductive replication in chicken embryo fibroblasts (CEF), but no capability of reproductive replication in the human keratinocyte cell line HaCat (Boukamp et al (1988), J. Cell Biol. 106:761-771), the human bone osteosarcoma cell line 143B (ECACC Deposit No. 91112502), the human embryo kidney cell line 293 (ECACC Deposit No. 85120602), and the human cervix adenocarcinoma cell line HeLa (ATCC Deposit No. CCL-2). Additionally, a derivative or variant of MVA-BN has a virus amplification ratio at least two fold less, more preferably threefold less than MVA-575 in Hela cells and HaCaT cell lines. Tests and assay for these properties of MVA variants are described in WO 02/42480 (U.S. Patent application No. 2003/0206926) and WO 03/048184 (U.S. Patent application No. 2006/0159699).

The term "not capable of reproductive replication" or "no capability of reproductive replication" is, for example, described in WO 02/42480, which also teaches how to obtain MVA having the desired properties as mentioned above. The term applies to a virus that has a virus amplification ratio at 4 days after infection of less than 1 using the assays described in WO 02/42480 or in U.S. Pat. No. 6,761,893.

The term "fails to reproductively replicate" refers to a virus that has a virus amplification ratio at 4 days after infection of less than 1. Assays described in WO 02/42480 or in U.S. Pat. No. 6,761,893 are applicable for the determination of the virus amplification ratio.

The amplification or replication of a virus is normally expressed as the ratio of virus produced from an infected cell (output) to the amount originally used to infect the cell in the first place (input) referred to as the "amplification ratio". An amplification ratio of "1" defines an amplification status where the amount of virus produced from the infected cells is the same as the amount initially used to infect the cells, meaning that the infected cells are permissive for virus infection and reproduction. In contrast, an amplification ratio of less than 1, i.e., a decrease in output compared to the input level, indicates a lack of reproductive replication and therefore attenuation of the virus.

For generation of a recombinant MVA as described herein any of the above MVA can be used. In a preferred embodiment, the MVA used for generating the recombinant virus is MVA or a derivative or variant thereof (in particular MVA-BN or a derivative or variant thereof), preferably having the capability of reproductive replication in vitro in chicken embryo fibroblasts (CEF) cells, but no capability of reproductive replication in the human keratinocyte cell line HaCat.

In another embodiments, the MVA used for generating the recombinant virus is MVA or a derivative or variant thereof (in particular MVA-BN or a derivative or variant thereof) having the capability of reproductive replication in vitro in chicken embryo fibroblasts (CEF) cells, but no capability of reproductive replication in the human keratinocyte cell line HaCat, the human bone osteosarcoma cell line 143B, and/or the human cervix adenocarcinoma cell line HeLa.

In another embodiment, the MVA used for generating the recombinant virus is MVA or a derivative or variant thereof (in particular MVA-BN or a derivative or variant thereof) having the capability of reproductive replication in vitro in chicken embryo fibroblasts (CEF) cells, but no capability of reproductive replication in the human keratinocyte cell line HaCat, the human bone osteosarcoma cell line 143B, the human embryo kidney cell line 293, and/or the human cervix adenocarcinoma cell line HeLa.

In another aspect, a MVA used for generating the recombinant virus may be MVA-572, MVA-575, Acamb3000 MVA, MVA-BN as deposited at the European Collection of Animal Cell cultures (ECACC) under accession number V00083008 or any similarly attenuated MVA strain.

In another embodiment, the MVA used for generating the recombinant MVA is MVA-BN as deposited at the European Collection of Animal Cell cultures (ECACC) under accession number V00083008.

MVA useful for the present invention can be prepared using methods known in the art, for example such as those described in WO 2002/042480 and WO 2002/24224.

Integration Sites into MVA

Nucleotide sequences encoding for one or more protein(s) (e.g., structural proteins or structural polyproteins) of an EEV may be inserted into any suitable part of the virus or viral vector, in particular the viral genome of the recombinant MVA. Suitable parts of the recombinant MVA are non-essential parts of the MVA genome. Non-essential parts of the MVA genome may be intergenic regions or the known deletion sites 1-6 of the MVA genome. Alternatively or additionally, non-essential parts of the recombinant MVA can be a coding region of the MVA genome which is non-essential for viral growth. However, the insertion sites are not restricted to these preferred insertion sites in the MVA genome, since it is within the scope of the present invention that the promoter, expression cassette and/or nucleotide encoding for one, two three or more protein(s) (e.g., structural proteins or structural polyproteins) of an EEV as described herein may be inserted anywhere in the viral genome as long as it is possible to obtain recombinants that can be amplified and propagated in at least one cell culture system, such as Chicken Embryo Fibroblasts (CEF cells). Preferably, the nucleotide sequences encoding for one, two, three or more protein(s) (e.g., structural proteins or structural polyproteins) of an EEV may be inserted into one or more intergenic regions (IGR) of the MVA. The term "intergenic region" refers preferably to those parts of the viral genome located between two adjacent open reading frames (ORF) of the MVA virus genome, preferably between two essential ORFs of the MVA virus genome. In certain embodiments, the IGR is selected from IGR 07/08, IGR 44/45, IGR 64/65, IGR 88/89, IGR 136/137, and IGR 148/149. In certain embodiments, less than 5, 4, 3 or 2 IGRs of the recombinant MVA comprise nucleotide sequences encoding for one or more protein(s) (e.g., structural proteins or structural polyproteins) of an EEV. The number of insertion sites of MVA comprising nucleotide sequences encoding for one or more protein(s) (e.g., structural proteins or structural polyproteins) of an EEV can be 1, 2, 3, 4, 5, 6, 7, or more. In certain embodiments, the nucleotide sequences are inserted into 4, 3, 2, or fewer insertion sites. Preferably, two insertion sites are used, preferably IGR 44/45 and IGR 88/89. In certain embodiments, three insertion sites are used. Preferably, the recombinant MVA comprises at least 2, 3, 4, 5, 6, or 7 genes inserted into 2 or 3 insertion sites.

The nucleotide sequences may, additionally or alternatively, be inserted into one or more of the known deletion sites, i.e., deletion sites I, II, III, IV, V, or VI of the MVA genome. The term "known deletion site" refers to those parts of the MVA genome that were deleted through continuous passaging on CEF cells characterized at passage 516 with respect to the genome of the parental virus from which the MVA is derived from, in particular the parental chorioallantois vaccinia virus Ankara (CVA) e.g., as described in Meisinger-Henschel et al. (2007), Journal of General Virology 88:3249-3259. In certain embodiments, less than 5, 4, 3, or 2 of the known deletion sites of the recombinant MVA comprise nucleotide sequences encoding for one, two, three or more protein(s) (e.g., structural proteins or structural polyproteins) of an EEV as described herein.

The recombinant MVA viruses provided herein can be generated by routine methods known in the art. Methods to obtain recombinant MVAs or to insert exogenous coding sequences into a MVA genome are well known to the person skilled in the art. For example, methods for standard molecular biology techniques such as cloning of DNA, DNA and RNA isolation, Western blot analysis, RT-PCR and PCR amplification techniques are described in Molecular Cloning, A laboratory Manual 2nd Ed. (J. Sambrook et al., Cold Spring Harbor Laboratory Press (1989)), and techniques for the handling and manipulation of viruses are described in Virology Methods Manual (B. W. J. Mahy et al. (eds.), Academic Press (1996)). Similarly, techniques and know-how for the handling, manipulation and genetic engineering of MVA are described in Molecular Virology: A Practical Approach (A. J. Davison & R. M. Elliott (Eds.), The Practical Approach Series, IRL Press at Oxford University Press, Oxford, UK (1993), see, e.g., Chapter 9: Expression of genes by Vaccinia virus vectors) and Current Protocols in Molecular Biology (John Wiley & Son, Inc. (1998), see, e.g., Chapter 16, Section IV: Expression of proteins in mammalian cells using vaccinia viral vector).

For the generation of the various recombinant MVAs disclosed herein, different methods known to the person skilled in the art may be applicable. The DNA sequence to be inserted into the virus can be placed into an *E. coli* plasmid construct into which DNA homologous to a section of DNA of the MVA has been inserted. Separately, the DNA sequence to be inserted can be ligated to a promoter. The promoter-gene linkage can be positioned in the plasmid construct so that the promoter-gene linkage is flanked on both ends by DNA homologous to a DNA sequence flanking a region of MVA DNA containing a non-essential locus. The resulting plasmid construct can be amplified by propagation within *E. coli* bacteria and isolated. The isolated plasmid containing the DNA gene sequence to be inserted can be transfected into a cell culture, e.g., of chicken embryo fibroblasts (CEFs), at the same time the culture is infected with MVA. Recombination between homologous MVA DNA in the plasmid and the viral genome, respectively, can generate an MVA modified by the presence of foreign DNA sequences.

According to a preferred embodiment, a cell of a suitable cell culture as, e.g., CEF cells, can be infected with the MVA. The infected cell can be, subsequently, transfected with a first plasmid vector comprising a foreign or heterologous gene or genes, preferably under the transcriptional control of an expression control element. As explained above, the plasmid vector also comprises sequences capable of directing the insertion of the exogenous sequence into a selected part of the MVA genome. Optionally, the plasmid vector also contains a cassette comprising a marker and/or selection gene operably linked to a poxvirus promoter. Suitable marker or selection genes are, e.g., the genes encoding the green fluorescent protein, β-galactosidase, neomycin-phosphoribosyltransferase or other markers. The use of selection or marker cassettes simplifies the identification and isolation of the generated recombinant MVA.

However, a recombinant MVA can also be identified by PCR technology. Subsequently, a further cell can be infected with the recombinant MVA obtained as described above and transfected with a second vector comprising a second foreign or heterologous gene or genes. In case, this gene shall be introduced into a different insertion site of the MVA genome, the second vector also differs in the MVA-homologous sequences directing the integration of the second foreign gene or genes into the genome of the MVA. After homologous recombination has occurred, the recombinant virus comprising two or more foreign or heterologous genes can be isolated. For introducing additional foreign genes into the recombinant virus, the steps of infection and transfection can be repeated by using the recombinant virus isolated in previous steps for infection and by using a further vector comprising a further foreign gene or genes for transfection.

Alternatively, the steps of infection and transfection as described above are interchangeable, i.e., a suitable cell can at first be transfected by the plasmid vector comprising the foreign gene and, then, infected with the MVA. As a further alternative, it is also possible to introduce each foreign gene into different viruses, co-infect a cell with all the obtained recombinant viruses and screen for a recombinant including all foreign genes. A third alternative is ligation of DNA genome and foreign sequences in vitro and reconstitution of the recombined vaccinia virus DNA genome using a helper virus. A fourth alternative is homologous recombination in *E. coli* or another bacterial species between a vaccinia virus genome cloned as a bacterial artificial chromosome (BAC) and a linear foreign sequence flanked with DNA sequences homologous to sequences flanking the desired site of integration in the vaccinia virus genome.

Expression of EEV Proteins

In certain embodiments, expression of one, more, or all of the nucleotide sequences encoding for a protein (e.g., a structural protein or structural polyprotein of any of the embodiments as described herein) of the EEV virus of any of the preferred EEVs (e.g., WEEV, VEEV, EEEV) as described herein is under the control of one or more poxvirus promoters. The promoter according to the present invention may be any synthetic or natural poxvirus promoter. In certain embodiments, the poxvirus promoter is a Pr13.5 promoter, a PrHyb promoter, a Pr7.5 promoter, a hybrid early/late promoter, a PrS promoter, a PrS5E promoter, a synthetic or natural early or late promoter, or a cowpox virus ATI promoter. Suitable promoters are further described in WO 2010/060632, WO 2010/102822, WO 2013/189611 and WO 2014/063832.

In certain embodiments, the poxvirus promoter is selected from the group consisting of the PrHyb promoter (SEQ ID NO:8) and the Pr13.5 promoter (SEQ ID NO:7).

A heterologous nucleotide sequence encoding for an EEV protein can be expressed as a single transcriptional unit. For example, a heterologous nucleotide sequence encoding an EEV protein (e.g., structural protein or structural polyprotein) can be operably linked to a poxvirus promoter and/or linked to a poxvirus (e.g., vaccinia virus) transcriptional terminator.

In certain embodiments, the transcriptional unit is inserted by itself into an insertion site in the MVA genome. In certain embodiments, the transcriptional unit is inserted with other transcriptional unit(s) into an insertion site in the MVA genome. The transcriptional unit is not naturally occurring (i.e., it is heterologous, exogenous or foreign) in the MVA genome and is capable of transcription in infected cells.

Preferably, the recombinant MVA comprises 1, 2, 3, 4, 5, or more transcriptional units inserted into the MVA genome. In certain embodiments, the recombinant MVA stably expresses heterologous nucleotide sequences encoding one, more, or all of the nucleotide sequences encoding for a structural protein or structural proteins (e.g., a structural protein or structural polyprotein of any of the embodiments as described herein) of a EEV virus of any of the preferred EEV (e.g., WEEV, VEEV, EEEV) encoded by 1, 2, 3, 4, 5, or more transcriptional units. In certain embodiments, the recombinant MVA comprises 2, 3, 4, 5, or more transcriptional units inserted into the MVA genome at 1, 2, 3, or more insertion sites in the MVA genome. In certain embodiments, the nucleotide sequence encoding the structural protein or structural polyproteins are transcribed at a similar transcription level and/or translated at a similar protein level e.g., as determined in Hela or Vero cells.

In further embodiments, the recombinant MVA of the invention comprises a nucleotide sequence for a transcriptional terminator, preferably a vaccinia early transcriptional terminator, preferably a TSNT sequence, more preferably a nucleotide sequence of TTTTTAT.

Further embodiments relate to the recombinant MVA comprising one, two or three nucleotide sequences each comprising a poxvirus promoter (preferably a poxvirus promoter selected from the group of Pr13.5 and PrHyb) operably linked to a nucleotide sequence encoding for a structural protein or structural polyprotein of the EEV excluding encoding for a capsid protein of the EEV, wherein the nucleotide sequences (preferably the two or three nucleotide sequences) encoding for the structural protein or structural polyproteins are transcribed at essentially the same transcription level and/or translated at essentially the same protein level.

Further embodiments relate to the recombinant MVA comprising one, two or three nucleotide sequences each comprising a poxvirus promoter (preferably a poxvirus promoter selected from the group of Pr13.5 and PrHyb) operably linked to a nucleotide sequence encoding for a structural protein or structural polyprotein of the EEV each excluding encoding for a capsid protein of the EEV, wherein the nucleotide sequences (preferably the two or three nucleotide sequences) encoding for the structural proteins or structural polyproteins having essentially the same expression level.

In certain embodiments, the recombinant MVA does not contain a viral replicon, in particular a viral replicon of an alphavirus e.g., of an EEV. In certain other embodiments, the recombinant MVA does not contain a viral replicon selected from the group of WEEV, EEEV and/or VEEV.

In other embodiments, the recombinant MVA does not contain a 26S promoter, preferably a 26S promoter of an alphavirus, more preferably a 26S promoter of an equine encephalitis virus, most preferably a 26S promoter of WEEV, EEEV and/or VEEV.

Composition, Pharmaceutical Compositions and Vaccines

Since the recombinant MVA viruses described herein are highly replication restricted in mammals, including MVA-BN which is also replication incompetent in human cell lines, they are ideal candidates for the treatment of a wide range of mammals including humans and even immune-compromised humans. Hence, provided herein are compositions (preferably pharmaceutical or immunogenic compositions) and vaccines comprising the recombinant MVAs according to the present invention e.g., for use as active pharmaceutical substances, all intended for inducing an immune response in a living animal body, including a human. The composition, vaccine and pharmaceutical composition as used herein may comprise a pharmaceutical acceptable carrier, expedient, or vehicle. In certain embodiments, the vaccine is di- or trivalent. In certain embodiments, the vaccine preferably pharmaceutical vaccine, comprises one, two, or more recombinant MVA each comprising a poxvirus promoter operably linked to a nucleotide sequence encoding for a structural protein or structural polyprotein of the EEV as described herein excluding encoding for a capsid protein of the EEV, preferably wherein each recombinant MVA encodes for a different EEV selected from the group of WEEV, EEEV and VEEV.

For this, the recombinant MVA, vaccine or pharmaceutical/immunogenic composition can be formulated in solution in a concentration range of $10^4$ to $10^9$ TCID$_{50}$/ml, $10^5$ to $5 \times 10^8$ TCID$_{50}$/ml, $10^8$ to $10^8$ TCID$_{50}$/ml, or $10^7$ to $10^8$ TCID$_{50}$/ml. A preferred vaccination dose for humans comprises between $10^8$ to $10^9$ TCID$_{50}$, including a dose of $10^8$ TCID$_{50}$, $10^7$ TCID$_{50}$, or $10^8$ TCID$_{50}$. Preferably, the dose for humans comprises at least $2 \times 10^7$ TCID$_{50}$, at least $3 \times 10^7$ TCID$_{50}$, at least $5 \times 10^7$ TCID$_{50}$, at least $1 \times 10^8$ TCID$_{50}$, at least $2 \times 10^8$ TCID$_{50}$, preferably in a volume of 0.1 to 0.5 ml.

The pharmaceutical/immunogenic compositions provided herein may generally include one or more pharmaceutically acceptable and/or approved carriers, additives, antibiotics, preservatives, adjuvants, diluents and/or stabilizers. Such auxiliary substances can be water, saline, glycerol, ethanol, wetting or emulsifying agents, pH buffering substances, or the like. Suitable carriers are typically large, slowly metabolized molecules such as proteins, polysaccharides, polylactic acids, polyglycolic acids, polymeric amino acids, amino acid copolymers, lipid aggregates, or the like.

For the preparation of vaccines and compositions (e.g., pharmaceutical compositions), the recombinant MVA viruses provided herein can be converted into a physiologically acceptable form. This can be done based on experience in the preparation of poxvirus vaccines used for vaccination against smallpox as described by H. Stickl et al., *Dtsch. med. Wschr.* 99:2386-2392 (1974).

For example, purified viruses can be stored at $-80°$ C. with a titer of $5 \times 10^8$ TCID$_{50}$/ml formulated in about 10 mM Tris, 140 mM NaCl pH 7.4. For the preparation of vaccine shots, e.g., $10^2$-$10^8$ or $10^2$-$10^9$ particles of the virus can be lyophilized in 100 ml of phosphate-buffered saline (PBS) in the presence of 2% peptone and 1% human albumin in an ampoule, preferably a glass ampoule. Alternatively, the vaccine shots can be produced by stepwise freeze-drying of the virus in a formulation. This formulation can contain additional additives such as mannitol, dextran, sugar, glycine, lactose or polyvinylpyrrolidone or other aids such as antioxidants or inert gas, stabilizers or recombinant proteins (e.g., human serum albumin) suitable for in vivo administration. A typical virus containing formulation suitable for freeze-drying comprises 10 mM Tris-buffer, 140 mM NaCl, 18.9 g/l Dextran (MW 36,000-40,000), 45 g/l Sucrose, 0.108 g/l L-glutamic acid mono potassium salt monohydrate pH 7.4. The glass ampoule is then sealed and can be stored between 4° C. and room temperature for several months. However, as long as no need exists, the ampoule is stored preferably at temperatures at or below $-20°$ C.

For vaccination or therapy, the lyophilisate can be dissolved in an aqueous solution (e.g., 0.1 to 0.5 ml), preferably water for injection, physiological saline or Tris buffer, and administered either systemically or locally, i.e., parenteral, subcutaneous, intravenous, intramuscular, intranasal, or any other path of administration known to the skilled practitioner. The mode of administration, the dose and the number of administrations can be optimized by those skilled in the art in a known manner.

The vaccines, compositions and methods described herein may also be used as part of a homologous prime-boost regimen. In the homologous prime-boost, a first priming vaccination is given followed by one or more subsequent boosting vaccinations. The boosting vaccinations are configured to boost the immune response generated in the first vaccination by administration of the same recombinant poxvirus that was used in the first vaccination.

In one exemplary embodiment a homologous prime-boost regimen may be employed wherein a MVA viral vector as defined herein is administered in a first dosage. One or more subsequent administrations of an MVA viral vector as defined herein can be given to boost the immune response provided in the first administration. Preferably, the one or more antigens delivered by the recombinant MVA are the same or similar to those of the first administration.

Kits Comprising Recombinant MVA

Also provided herein are kits comprising the recombinant MVA, and/or the composition, and/or the vaccine comprising the recombinant MVA of the present invention in a first vial or container for a first administration (priming) and in a second vial or container for a second administration (boosting).

Another aspect of the invention relates to a kit comprising the recombinant MVA, and/or the composition, and/or the vaccine comprising the recombinant MVA of the present invention in a first vial or container for priming an immune response and in a second vial or container for boosting the immune response.

The kit can comprise one or multiple containers or vials of the recombinant MVA, together with instructions for the administration of the recombinant MVA to a subject at risk of an EEV infection, preferably a WEEV, VEEV and/or EEEV infection. In certain embodiments, the subject is a human. The instructions may indicate that the recombinant MVA is administered to the subject in a single dose, or in multiple (i.e., 2, 3, 4, etc.) doses.

Another aspect of the invention relates to a kit comprising the recombinant MVA of the present invention, and/or the composition, and/or the vaccine comprising the recombinant MVA of the present invention comprising at least two vials or containers wherein each vial comprises a recombinant MVA comprising a nucleotide sequence encoding for a different structural protein or structural polyprotein of the equine encephalitis virus (EEV) selected from the group of WEEV, VEEV and EEEV.

The kit may also comprise the recombinant MVA in a third, fourth or further vial or container for a third, fourth or further administration.

Method and Uses of the Recombinant MVA

Also provided herein are recombinant MVAs, compositions, and/or vaccines comprising the recombinant MVA for use as a medicament or vaccine.

A further aspect of the present invention relates to the recombinant MVA of the present invention, and/or the composition, and/or the vaccine comprising the recombinant MVA of the present invention for manufacturing of a vaccine for treating and/or preventing an equine encephalitis virus caused disease, preferably a Venezuelan, western and/or eastern equine encephalitis virus caused disease.

A further aspect of the present invention relates to the recombinant MVA of the present invention, the composition, and/or the vaccine comprising the recombinant MVA of the present invention for use in treating and/or preventing an equine encephalitis virus caused disease, preferably a Venezuelan, western and/or eastern equine encephalitis virus caused disease.

In preferred embodiments, the recombinant MVA for use as a medicament or vaccine or for manufacturing of a vaccine for treating and/or preventing an equine encephalitis virus caused disease (preferably a Venezuelan, western and/or eastern equine encephalitis virus caused disease) or for use in treating and/or preventing an equine encephalitis virus caused disease (preferably a Venezuelan, western and/or eastern equine encephalitis virus caused disease), the composition, or the vaccine is administered once, twice, three times or four times.

Certain embodiments, relate to the use of the recombinant MVA, the composition, or the vaccine comprising the recombinant MVA as provided herein for manufacturing of a vaccine for treating and/or preventing an equine encephalitis virus caused disease, preferably a Venezuelan, western and/or eastern equine encephalitis virus caused disease.

In certain embodiments, any of the recombinant MVAs, vaccine or pharmaceutical composition comprising the recombinant MVA as provided herein are administered to the subject at a dose of $10^6$ to $10^9$ $TCID_{50}$, at a dose of $10^6$ to $5 \times 10^8$ $TCID_{50}$, or $10^7$ to $10^8$ $TCID_{50}$. The recombinant MVAs provided herein may also be administered to the subject at a dose of $10^6$, $10^7$ $TCID_{50}$, $10^8$, or $5 \times 10^8$ $TCID_{50}$. In certain embodiments, any of the recombinant MVAs provided herein is administered to a human subject at a dose of $10^7$ $TCID_{50}$, $10^8$ $TCID_{50}$, or $5 \times 10^8$ $TCID_{50}$.

The recombinant MVAs, vaccine or pharmaceutical composition comprising the recombinant MVA provided herein are administered to the subject in a single dose, or in multiple (i.e., 2, 3, 4, etc.) doses. In certain embodiments, the recombinant MVAs are administered in a first (priming) and second (boosting) administration. In certain embodiments, the first dose comprises $10^7$ to $10^8$ $TCID_{50}$ of recombinant MVA virus and the second dose comprises $10^7$ to $10^8$ $TCID_{50}$ of recombinant MVA virus.

The recombinant MVAs, vaccine or pharmaceutical composition comprising the recombinant MVA can be administered systemically or locally, parenterally, subcutaneously, intravenously, intramuscularly, or intranasally, preferably intramuscularly or intranasally.

Certain embodiments, relate to the use of the recombinant MVA, the composition, or the vaccine comprising the recombinant MVA as provided herein for manufacturing of a vaccine for treating and/or preventing an equine encephalitis virus caused disease, preferably a Venezuelan, western and/or eastern equine encephalitis virus caused disease.

Another aspect of the present invention relates to a method for affecting an immune response in a subject comprising administering to the subject the recombinant MVA of the present invention, and/or the composition, and/or the vaccine comprising the recombinant MVA of the present invention, preferably wherein the recombinant MVA is administered once, twice, three times or four times.

Another aspect of the present invention relates to a method for treating and/or preventing in a subject an equine encephalitis virus caused disease, preferably an western, Venezuelan and/or eastern equine encephalitis virus caused disease in a subject comprising administering to the subject the recombinant MVA of the present invention, and/or the composition, and/or the vaccine comprising the recombinant MVA of the present invention, preferably wherein the recombinant MVA is administered once, twice, three times or four times.

In particular, the following embodiments are provided by the present invention:

1. A recombinant modified vaccinia virus Ankara (MVA) comprising a nucleotide sequence of a poxvirus promoter operably linked to a nucleotide sequence encoding for a structural protein, preferably a structural polyprotein, of an equine encephalitis virus (EEV) excluding encoding for a capsid protein of the EEV.
2. The recombinant MVA of embodiment 1, wherein the EEV is selected from the group of western equine encephalitis virus (WEEV), Venezuelan equine encephalitis (VEEV) and/or eastern equine encephalitis virus (EEEV).
3. The recombinant MVA of embodiment 1, wherein the nucleotide sequence encoding for the structural protein or structural polyprotein is derived from one or more western equine encephalitis virus (WEEV).
4. The recombinant MVA of embodiment 1, wherein the nucleotide sequence encoding for the structural protein or structural polyprotein is derived from one or more Venezuelan equine encephalitis virus (VEEV).
5. The recombinant MVA of embodiment 1, wherein the nucleotide sequence encoding for the structural protein or structural polyprotein is derived from one or more eastern equine encephalitis virus (EEEV).
6. The recombinant MVA of embodiment 3, further comprising a nucleotide sequence encoding for a structural protein or structural polyprotein selected from the group consisting of Venezuelan (VEEV) and/or eastern equine encephalitis virus (EEEV).
The recombinant MVA of embodiment 4, further comprising a nucleotide sequence encoding for a structural protein or structural polyprotein selected from the group consisting of western (WEEV) and/or eastern equine encephalitis virus (EEEV).
8. The recombinant MVA of embodiment 5, further comprising a nucleotide sequence encoding for a structural protein or structural polyprotein selected from the group consisting of western (WEEV) and/or Venezuelan equine encephalitis virus (VEEV).
9. The recombinant MVA of any one of embodiments 1 to 8, wherein the nucleotide sequence encodes a structural protein or structural polyprotein comprising E3, E2, 6k and E1, preferably comprising solely E3, E2, 6k and E1 more preferably consisting of E3, E2, 6k and E1.
10. The recombinant MVA of any one of embodiments 1 to 9, wherein the nucleotide sequence of the structural protein or structural polyprotein is selected from strain CBA87, 71V-1658, FL93-939, Fleming, TrD, INH-9813, INH-6803, 71V-1658, PE-6, FL91-4679, and/or V105-00210, preferably FL93-939, TrD, Fleming and/or V105-00210.
11. The recombinant MVA of any one of embodiments 1 to 10, wherein the nucleotide sequence of the structural protein or structural polyprotein is selected from strain CBA87, 71V-1658, FL93-939, and/or Fleming.
12. The recombinant MVA of any one of embodiments 1 to 11, wherein the nucleotide sequence encoding for the structural protein or structural polyprotein encodes the amino acid sequence of SEQ ID NO: 1, 2 and/or 3.
13. The recombinant MVA of any one of embodiments 1 to 12, wherein the nucleotide sequence encoding for the structural protein or structural polyprotein is selected from the group of SEQ ID NO: 4, 5, and/or 6.
14. The recombinant MVA of any one of embodiments 1 to 14, wherein the promoter is selected from the group consisting of Pr13.5 and PrHyb.
15. The recombinant MVA of any one of embodiments 1 to 14, comprising a nucleotide sequence for a transcriptional terminator, preferably a vaccinia early a transcriptional terminator, preferably a T5NT sequence, more preferably a nucleotide sequence of TTTTTAT.
16. The recombinant MVA of any one of embodiments 1 to 15, wherein the nucleotide sequence is selected from the group of SEQ ID NO: 4, 5, 6, 7, and/or 8.
17. The recombinant MVA of any one of embodiments 1 to 16, wherein the nucleotide sequence is inserted into an intergenic region (IGR), preferably IGR 44/45 and/or 88/89.
18. The recombinant MVA of any one of embodiments 1 to 17, wherein the nucleotide sequence of the structural protein or structural polyprotein is not expressed from a viral replicon.
19. The recombinant MVA of any one of embodiments 1 to 18, wherein the MVA does not contain a 26S promoter, preferably a 26S promoter of an alphavirus, more preferably a 26S promoter of an equine encephalitis virus, most preferably a 26S promoter of WEEV, EEEV and/or VEEV.
20. The recombinant MVA of any one of embodiments 1 to 19, wherein the MVA is an MVA-BN virus or derivative having the capability of reproductive replication in vitro in chicken embryo fibroblasts (CEF) cells, but no capability of reproductive replication in the human keratinocyte cell line HaCat, the human bone osteosarcoma cell line 143B, the human embryo kidney cell line 293, and the human cervix adenocarcinoma cell line HeLa.
21. The recombinant MVA of any one of embodiments 1 to 20, wherein the MVA is MVA-BN as deposited at the European Collection of Animal Cell cultures (ECACC) under accession number V00083008.
22. A composition comprising the recombinant MVA of any one of embodiments 1 to 21 and a pharmaceutical acceptable carrier, excipient, or vehicle.
23. The composition of embodiment 22, wherein the composition is a pharmaceutical composition.
24. A vaccine or cell comprising the recombinant MVA of any one of embodiments 1 to 21.
25. A vaccine comprising two or three recombinant MVA of any one of embodiments 1 to 21.
26. The vaccine of embodiment 25, wherein the vaccine is trivalent.
27. A kit comprising the recombinant MVA of any one of embodiments 1 to 21, and/or the composition of embodiments 22 to 23, and/or the vaccine of any one of embodiments 24 to 26 in a first vial or container for a first administration (priming) and in a second vial or container for a second administration (boosting).
28. A kit comprising the recombinant MVA of any one of embodiments 1 to 21, and/or the composition of embodiments 22 or 23, and/or the vaccine of any one of embodiments 24 to 26 comprising at least two vials or containers wherein each vial comprises a recombinant MVA comprising a nucleotide sequence encoding for a different structural protein or structural polyprotein of the equine encephalitis virus (EEV) selected from the group of WEEV, VEEV and EEEV.
29. The kit of embodiments 27 or 28, comprising in a third, fourth or further vial or container a recombinant MVA for a third, fourth or further administration.
30. The recombinant MVA of any one of embodiments 1 to 21, and/or the composition of any one of embodiments 22 or 23, and/or the vaccine of any one of embodiments 24 to 26 for use as a medicament or vaccine.
31. The recombinant MVA of any one of embodiments 1 to 21, and/or the composition of any one of embodiments 22 or 23, and/or the vaccine of any one of embodiments 24 to 26 for use in the treatment and/or prevention of an equine encephalitis virus caused disease, preferably a Venezuelan, western and/or eastern equine encephalitis virus caused disease.

32. The use of the recombinant MVA of any one of embodiments 1 to 21, the composition of embodiments 22 or 23, or the vaccine of any one of embodiments 24 to 26 for manufacturing of a vaccine for treating and/or preventing an equine encephalitis virus caused disease, preferably a Venezuelan, western and/or eastern equine encephalitis virus caused disease.

33. A method for affecting an immune response in a subject comprising administering to the subject the recombinant MVA of any one of embodiments 1 to 21, the composition of embodiment 22 or 23, or the vaccine of any one of embodiments 24 to 26, preferably wherein the recombinant MVA is administered once, twice, three times or four times.

34. A method for treating and/or preventing in a subject an equine encephalitis virus caused disease, preferably a western, Venezuelan and/or eastern equine encephalitis virus caused disease, comprising administering to the subject the recombinant MVA of any one of embodiments 1 to 21, the composition of embodiment 22 or 23, or the vaccine of any one of embodiments 24 to 26, preferably wherein the recombinant MVA is administered once, twice, three times or four times.

35. The recombinant MVA for use according to embodiments 30 or 31, the use of the recombinant MVA of embodiments 32 or the composition of embodiment 22 to 23, wherein the recombinant MVA of any one of embodiments 1 to 19, the composition of embodiments 22 or 23, or the vaccine of any one of embodiments 24 to 26 is to be administered once, twice, three times or four times.

EXAMPLES

The detailed examples which follow are intended to contribute to a better understanding of the present invention. However, the invention is not limited by the examples. Other embodiments of the invention will be apparent to those skilled in the art from consideration of the specification and practice of the invention disclosed herein.

Example 1: Viruses and Mice

The following viruses were used in the studies: VEEV subtype IAB (strain TrD), WEEV (strain Fleming, 71V-1658), EEEV (strain PE-6). The 71V-1658 strain of WEEV contained in a 10 percent suckling mouse brain suspension was provided as previously described in WO 2008/101349 by Nick Karabatsos (CDC, Fort Collins, Colo.). The Fleming strain was purchased from ATCC. Seed stocks of WEEV were made by the inoculation of Vero cells with the mouse brain suspension at a multiplicity of infection (MOI) of less than 0.1. The supernatant of the infected cells was collected, aliquoted, and stored at −80 degrees centigrade for further use in animal challenge studies and plaque reduction neutralization assays. The EEEV PE-6 strain (Platteborze (2005), DNA Seq. 16:308-20; Maire et al. (1970), The American Journal of Tropical Medicine and Hygiene 19:119-22) was kindly provided by George Ludwig (USAMRIID, Frederick, Md.) as a Vero cell lysate. Seed stocks of EEEV PE-6 were made by the inoculation of Vero cells with the lysate at a multiplicity of infection (MOI) of less than 0.1. The supernatant of the infected cells was collected, aliquoted, and stored at −80 degrees centigrade for further use in animal challenge studies and plaque reduction neutralization assays. VEEV TrD (Kinney at al. (1989), Virology 170:19-30) was purchased from ATCC as a freeze-dried aliquot. After rehydration, seed stocks of VEEV TrD were made by the inoculation of Vero cells with the lysate at a multiplicity of infection (MOI) of less than 0.1. The lysate was then used to inoculate the brains of suckling mice (10 µl per mouse brain), and a 10% suckling mouse brain suspension was collected, clarified, aliquoted, and stored at −80 degrees centigrade for further use in animal challenge studies and plaque reduction neutralization assays. For exposures, viruses were diluted to the appropriate concentration in HBSS.

Female BALB/c mice (15-18 g) were purchased from Charles River Canada. All the procedures for mouse experiments were approved by the Animal Committee at DRDC Suffield and complied with guidelines set by the Canadian Council on Animal Care.

Example 2: Sequences Used for Vaccine Generation

The viral strains used for vaccine development were FL93-939 (NA) encoding for the amino acid sequence of sequence EF151502.1 (EEEV), Trinidad (TrD) encoding for the amino acid sequence of sequence L01442.2 (VEEV), 71V-1658 encoding for the amino acid sequence of sequence GQ287645.1 (WEEV). The used transgenes for the EEEV, VEEV and WEEV were designed such as to encode for the structural proteins (E3, E2, 6K and E1, SEQ ID NOs: 1, 2, and 3) not including the capsid protein (CP) which encapsidates the genomic RNA to form the nucleocapsid core as they can be considered to be the primary targets for the adaptive immunity and to avoid interfering with host defense mechanisms.

The genes encoding the structural proteins E3-E2-6K-E1 were optimized using GeneOptimizer™ (Genart GmbH; Regensburg). This included codon usage adaptation and optimization for mammalian expression. In addition, the sequences were optimized to reduce homology between the different transgenes.

Example 3: MVA Virus Expressing WEEV, VEEV and EEEV Antigens

All recombinant virus vectors used for the studies as described herein were based on MVA-BN® developed by Bavarian Nordic which is deposited at the European Collection of Cell Cultures (ECACC) (V00083008). The generation of MVA recombinants was carried out according to a method recently described (WO 2012/048817). However, also the method as described in Baur et. al. and Lauterbach et al. is suitable for generating the recombinant viruses of the present invention (Baur et al. (2010), J. Virol 84:8743-8752; Lauterbach et al. (2013), Front Immunol. 4:251).

MVA constructs were prepared to express the optimized sequences under the control of the promoter Pr13.5 (SEQ ID NO:7) or PrHyb (SEQ ID NO:8) as described in WO 2014/063832 or Baur et al. (Baur et al. (2010), J. Virol 84:8743-8752) followed by a vaccinia virus transcriptional terminator T5AT (TTTTTAT).

For the insertion of foreign genes into the MVA genome several recombination plasmids that target intergenic regions (IGR) of the MVA genome were generated. To generate recombinant MVA products, foreign sequences of interest were inserted into any of these basic vectors, e.g., pBNX202 targeting IGR 88/89 consisting of either one of two or both expression cassettes (see FIG. 1) of SEQ ID NO:1 for the WEEV coding sequence with an upstream Pr13.5 promoter (SEQ ID NO:7) and SEQ ID NO:2 for the VEEV coding sequence with the upstream promoter PrHyb (SEQ ID NO:8) directly upstream of the first "ATG" and a vaccinia transcriptional terminator TTTTTAT or pBNX208 targeting IGR 44/45 consisting of an expression cassette of Pr13.5 (SEQ ID NO:7) followed by the EEEV coding sequence (SEQ ID NO:3) and a vaccinia virus transcriptional terminator (TTTTTAT) using commonly available restriction enzymes and conventional molecular biology techniques.

To insert the EEV transgenes into MVA, CEF cells were infected with MVA and subsequently transfected with the recombination plasmids. During homologous recombination, the MVA-derived sequences within the plasmid, flanking the transgene sequences (termed flanking regions), recombine with their homologous sequences in the MVA genome targeting and inserting the transgenes to their specific IGR within the virus (e.g., IGR 44/45 or IGR 88/89 of the MVA genome). After amplification and plaque purification under selective conditions (mycophenolic acid/xanthine and hypoxanthine or Geneticin) the recombinant MVA products designated MVA PreMaster containing the individual genes for EEV were obtained. Intermediate passages and clones as well as the recombinant MVA PreMaster virus stock were examined for elimination of MVA (purity), for correct sequence of the inserted genes together with the insertion flanking regions (by sequencing), and for the presence (by EEV gene-specific PCR) and correct size of the inserts (using primers specific for the MVA genomic sequences flanking the IGR used during insertion of the foreign EEV genes).

Research grade product was produced in CEF cells and purified and concentrated in a standardized two step sucrose cushion centrifugation procedure. The final product was formulated in Tris buffered saline, TBS.

Example 4: Antigen Expression (FACS)

Expression of the structural proteins of the recombinant MVA viruses were analyzed in HeLa cells (ATCC, passage <50) by FACS analysis using standard methods. In brief, HeLa cells were infected with 10 $TCID_{50}$ per cell; surface staining was performed 20 hrs p.i. with antibodies that were specific for the respective vaccine antigens (WEEV, EEEV or VEEV respectively). Anti-EEEV polyclonal mouse (from mouse ascites, ATCC VR1242AF, by NIAID, USA) was protein G affinity purified in accordance to the manufacturer's instructions. After purification and pooling of the antibody containing fractions, the antibody (1:500) was used to detect the expression of structural proteins on the surface of cells infected with recombinant MVA containing an expression cassette of the E3-E2-6k-E1 protein(s) of EEEV. The monoclonal mouse anti-WEEV antibody (clone 11D2, DRDC, protein G purified, 1:2000) against the E1 of WEEV strain B11 was used to detect the expression of the E1 protein expressed from recombinant MVA containing an expression cassette of the E3-E2-6k-E1 protein(s) of WEEV. The monoclonal mouse anti-VEEV antibody (clone 1A4A1, DRDC, 1:2000) against the E2 protein was used to detect the expression of the E2 protein expressed from recombinant MVA containing an expression cassette of the E3-E2-6k-E1 protein(s) of VEEV. A goat anti-mouse antibody conjugated to APC (Jackson Immuno Research Laboratories Inc., 115-136-146, 1:500) was used as secondary detection antibody. Infected HeLa cells were additionally stained with DAPI for live/dead discrimination. The stained cells were gated on live and infected cells (RFP+ or GFP+ cells). FACS analysis was performed on a FACS LSR II (Becton Dickinson). FACS results are shown in FIGS. 3A and 3B.

Example 5: Study Protocol and Immunization (Lethal Murine i.n. Challenge Model)

To evaluate the protective efficacy against EEEV, VEEV and WEEV in a lethal challenge model female BALB/c mice (5 per group) were immunized with two doses ($1\times10^8$ $TCID_{50}$ per dose) at 0 and 28 days using the subcutaneous route of inoculation (VEEV, WEEV, EEEV or triple immunization with VEEV, WEEV and EEEV) and the intramuscular route of application (VEEV). A minimum of 50 µL (max 150 µL) were applied per mouse, if necessary the vaccine was diluted with HBSS (Hank Balanced Salt Solution, Gibco 14175-095). For each virus strain tested, a HBSS control group, a MVA group and a MVA-EEEV, MVA-WEEV or MVA-VEEV group was challenged with the same strain of virus, WEEV 71V-1658, Fleming, EEEV PE-6 or VEEV TrD, respectively. Blood samples were drawn by tail vein sampling at −1 day, 14 days and 41 days post inoculation. Challenge was done at 42 days post-inoculation by IN (intranasal) application of 1,000/5,000/10,000 pfu of WEEV (Fleming or 71V-1658), EEEV (PE-6) or VEEV (TrD).

For virus challenge, sodium pentobarbital at 50 mg/kg diluted in sterile PBS was given i.p. The virus suspension of WEEV 71V-1658, EEEV PE-6 or VEEV TrD (1,000, 5,000 and 10,000 pfu) was applied to the nostrils of the unconscious mouse using a micropipette in a total volume of 50 µL HBSS. The mice were monitored daily for signs and symptoms for 14 days. The animals were followed-up for weight loss and disease scoring. Mice showing strong signs of morbidity were euthanized.

A similar protocol as designed for the trivalent immunization with a mixture of three different monovalent MVA was designed for analysis of a single multivalent construct MVA-EEEV/WEEV/VEEV (MVA-mBN396A) expressing the three structural proteins of EEEV, WEEV and VEEV as used for the single constructs in one MVA (FIG. 1). Animals were vaccinated according to the same protocol as mentioned above with a dose of $3.6\times10^7$ $TCID_{50}$ (FIG. 6) or $1\times10^8$ $TCID_{50}$ in a volume of 150 µL of the trivalent MVA-mBN396A.

For results see example 6 and FIGS. 2A, 2B, 2C, 6 and 7.

Example 6: Survival Rates

Complete survival was seen with administration of the highest dose (10,000 pfu) as well as lowest dose (1,000 pfu) of virus challenge after immunization with MVA-VEEV and MVA-WEEV and challenge (intranasal challenge) with VEEV TrD or WEEV 71V-1658 but also with the lower dose of 1,000 pfu of EEEV PE-6 (100%) with a dose dependent decline in survival seen at higher doses with 5,000 pfu EEEV PE-6 (80%) or 10,000 pfu (75%). Exemplary results are shown in FIGS. 2A, 2B, and 2C. In a repeat study 100% (5/5) survival could be observed with 5,000 pfu EEEV PE-6 challenge (FIG. 6). For MVA-VEEV, the immunization routs of SC and IM were compared. No significant difference was observed between the two routes of administration. Both gave 100% protection against even a higher challenge dose of VEEV ($10^4$ pfu).

The benefits of these immunizations were significant above previous studies shown for vaccinia virus expressing structural VEEV proteins with only partial protection against respiratory challenge with virulent VEEV. In addition, full protection against the neurotropic western equine encephalitis virus could be shown even at high virus challenge with WEEV 71V-1658 (10,000 pfu). As the challenge virus of EEEV differed from the one used for cloning the structural proteins (FL93-939 (NA)) these data showed cross-protective immunity against a heterologous strain of EEEV (PE-6). These interesting results enabled further development of a trivalent alphavirus vaccine.

Since all the three single vaccines expressed the E3-E2-6K-E1 transgenes of EEEV, WEEV and VEEV respectively in equivalent amounts via FACS analysis, a mixture of three vaccines was compared to the single MVA alphavirus vaccine to examine if the triple mixture would reduce the effective efficacy. Thus, for assessment of the trivalent vaccination mice were immunized with two doses of vaccine ($1 \times 10^8$ $TCID_{50}$ per dose) at 0 and 28 days, using the subcutaneous route of inoculation in a total volume of 150 µL with HBSS as the diluent (each group 5 BALB/c mice). A mixture of the three vaccines (MVA-mBN393A, MVA-mBN394A and MVA-mBN395A, triple mixture) was assessed against the MVA-monovalent vaccines. An MVA vector without inserts was used as a control for each of the challenge virus strains, and HBSS control groups to assess immune stimulation of the vector alone were added. Blood samples were drawn by tail vein sampling at −1 day, 27 days and 41 days post inoculation for PRNT. Challenge was done at 42 days post-inoculation by respiratory (i.e., intranasal) application. For virus challenge the same protocol as described above for the single construct was used but using 5,000 pfu of the respective challenge strain. Blood samples were collected at 14 and 41 days. There was no difference between the survival of mice between the monovalent MVA and the triple mixture of the three vaccines when challenged with WEEV 71V-1658. Full protection was achieved against VEEV TrD (5/5, 100%) and WEEV Fleming challenge (5/5, 100%) in the MVA-EEEV/MVA-WEEV/MVA-VEEV triple mix group thus indicating that there is no negative interference between VEEV and WEEV when using recombinant MVA as a vaccine. These data also demonstrated fully cross-protection against the highly virulent heterologous strain Fleming, which differs in 21 amino acids from the amino acid sequence of the homologous WEEV strain 71V-1658, upon triple mix application of MVA-EEEV/MVA-WEEV/MVA-VEEV compared to 90% (9/10) upon single immunization with MVA-WEEV at 5,000 pfu. For EEEV, 3 of 5 animals survived (60%) against a heterologous challenge with EEEV PE-6.

In conclusion, it was found that the monovalent vaccine when given as a triple mixture encoding for structural proteins of EEEV/WEEV/VEEV excluding the capsid protein provided high protection against all three subtypes in BALB/c mice. Immunized mice demonstrated solid levels of protection against fairly significant intranasal doses of the appropriate challenge virus (1,000 to 10,000 pfu per mouse). The surviving mice showed no symptoms of infectivity or weight loss. Neutralizing antibodies were detected prior to challenge with the respective WEEV, EEEV and VEEV virus, but may not be the only mechanism of protection.

In FIGS. 6 and 7 results are shown using the single multivalent construct MVA-EEEV/WEEV/VEEV (MVA-mBN396A) expressing the three structural proteins of EEEV, WEEV and VEEV. Using only one third of the recombinant MVA dose ($3.6 \times 10^7$ $TCID_{50}$) as used for the monovalent MVA already provided 80% protection against the highly virulent TrD strain (FIGS. 6 and 7). Such a multivalent MVA-EEEV/WEEV/VEEV (MVA-mBN396A) provides the advantage of expressing all three antigens in one construct using a single recombinant MVA instead of mixing three recombinants or applying three constructs individually to protect against all three equine encephalitis viruses, which simplifies production of the product and reduces the production costs. It further enables immunization against the alphaviruses and the poxvirus at the same time enabling tetravalent immunization without immunodominance of one or more of the antigens or the vector.

These results suggest that recombinant MVA expressing for structural proteins of one, two or three EEVs (i.e., EEEV/WEEV/VEEV) could serve as a prophylactic vaccine against single or concurrent infection of EEEV, WEEV and VEEV in humans.

Example 7: Anti-Alphavirus Neutralizing Titers

Figure 4:
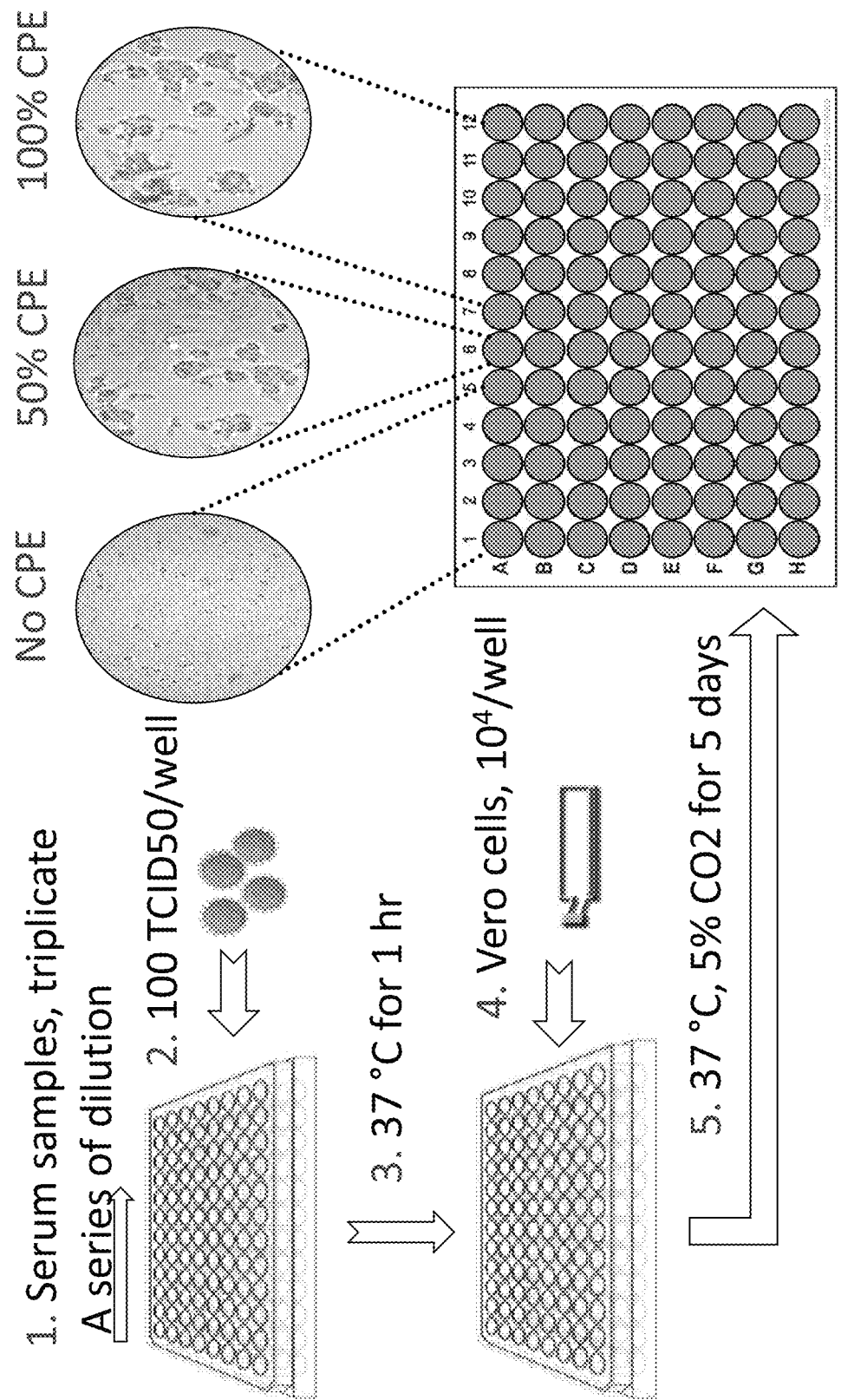
FIG. 4 shows a schematic overview of the serum anti-alphavirus neutralization titration assay as described in example 7.

In order to investigate the mechanism of protective efficacy of MVA-based alphavirus vaccines, the serum samples from vaccinated mice were evaluated for anti-alphavirus neutralizing titers. Serum samples were incubated for 30 min at 56° C. A series of dilutions was made in 96-well plates. 10 µL of each sample was added to the first well of 190 µL of DMEM 5% FBS to obtain a starting dilution of 1:20. Three-fold dilutions were made by pipetting 100 µL from each well to the next (200 µL 5% DMEM) and 50 µl were transferred to a new plate. 50 µl of virus (100 $TCID_{50}$) was added to each well. Thus, triplicates of pooled serum samples (12 serial dilutions) from mice (n=5) treated with recombinant MVA, MVA or HBSS as control mixed with 50 µl of virus (100 $TCID_{50}$) per well were incubated at 37° C. for 1 hour. 10,000 Vero cells ($10^4$ per well) were inoculated in DMEM 5% FBS with 50 µL of prediluted serum in 96 well plates and incubated at 37° C. 5% $CO_2$ for 5 days (FIG. 4). Cytopathic effects (CPE) were examined under the microscope. The neutralizing titer was defined as the reciprocal of the highest dilution of serum capable of neutralizing 100 $TCID_{50}$ of the virus e.g., TrD, Fleming, 71V-1658 or PE6. Results are shown in FIGS. 5A-5C.

In general, MVA-based single alphavirus vaccines did elicit anti-alphavirus neutralizing antibodies. An immunization booster increased the titers of neutralizing antibodies. However, the triple mixture of three vaccines only elicited neutralizing antibodies against WEEV Fleming and EEEV PE6, not against VEEV TrD but nevertheless protected against TrD. Although neutralizing antibodies play a pivotal role in protective efficacy against alphavirus in vivo, it is still controversial about the role of non-neutralizing antibodies in vivo. Some studies showed that non-neutralizing antibodies have anti-pathogen efficacy in vivo. On the other hand, MVA is good at eliciting both humoral and cell-mediated immunities. We cannot rule out the possibility that non-neutralizing antibodies or cell-mediated immunity might play a pivotal role in the MVA-based alphavirus vaccines against alphavirus infections and neutralizing antibodies might play a limited role.

Example 8: Vaccination in Cynomolgus Macaques by Aerosol Challenge

To analyze the efficacy of the recombinant MVAs an established model of nonhuman primates (cynomolgus macaques) has been previously described (Reed et al. (2007), J. Infect. Dis. 196:441-50; Reed et al. (2005), J. Infect. Dis. 192:1173-82; Steele and Twenhafel (2010), Vet. Pathol. 47:790-805). Before analysis blood samples will be screened for PRNT for any evidence of a previous exposure to VEEV, WEEV or EEEV. Exposure in this model is to apply the study material as an i.m. inoculation of the vaccine or control 2 times separated by 28 days with a dose of 5×10$^8$ TCID$_{50}$. On days 0, 7, 28, 35 and 49 PBMC are isolated. Blood samples are collected at day 0, 28 and 49 for analysis of antibody and PRNT. After 60 days macaques are anesthetized by injection of 6 mg/kg of Telazol and exposed for 10 min with aerosol as described by Reed et al. (Reed et al. (2004), J. Infect. Dis. 189:1013-1017) containing the virus challenge in a dose sufficient to cause a disease (e.g., 1×10$^8$ pfu). Post challenged animals are monitored daily for any signs of symptoms and illness.

Example 9: Analytical Methods

The examples herein can further be supported by methods to determine neutralizing antibody titers (e.g., plaque reduction neutralization titer (PRNT), Enzyme-linked immunosorbent assays (ELISA) and western blot) which are well known to those skilled in the art. See, for example, a method for Western blot and PRNT assay for WEEV as described in Wu et al. (Wu et al. (2007), Vaccine 25:4368-4375). For VEEV an ELISA, PRNT assay and Enzyme-Linked ImmunoSpot (ELISPOT) assay are described for example in Dupuy et al. (2011), Clinical and Vaccine Immunology 18:707-716. Methods for analysis of EEEV (plaque reduction neutralization titer (PRNT), Enzyme-linked immunosorbent assays (ELISA) and Western blotting) are described under Material and Methods in Reed et al. (Read et al. (2014), Journal of Virology 88:12077-12086).

Description of the Sequence Listing

SEQ ID NO:1—amino acid sequence of structural proteins of WEEV

SEQ ID NO:2—amino acid sequence of structural proteins of VEEV

SEQ ID NO:3—amino acid sequence of structural proteins of EEEV

SEQ ID NO:4—nucleic acid sequence of structural proteins of WEEV

SEQ ID NO:5—nucleic acid sequence of structural proteins of VEEV

SEQ ID NO:6—nucleic acid sequence of structural proteins of EEEV

SEQ ID NO:7—Pr13.5 promoter

SEQ ID NO:8—PrHyb promoter

We claim:

1. A recombinant modified vaccinia virus Ankara (MVA) comprising:
   (a) a poxviral promoter operably linked to a first nucleotide sequence encoding a structural polyprotein of an Eastern equine encephalitis virus, wherein the nucleotide sequence encoding the capsid protein for said virus is excluded;
   (b) a poxviral promoter operably linked to a second nucleotide sequence encoding a structural polyprotein of a Venezuelan equine encephalitis virus, wherein the nucleotide sequence encoding the capsid protein for said virus is excluded; and
   (c) a poxviral promoter operably linked to a third nucleotide sequence encoding a structural polyprotein of a Western equine encephalitis virus, wherein the nucleotide sequence encoding the capsid protein for said virus is excluded.

2. The recombinant MVA of claim 1, wherein said first nucleotide sequence encodes a structural polyprotein comprising E3, E2, 6k and E1.

3. The recombinant MVA of claim 1, wherein said second nucleotide sequence encodes a structural polyprotein comprising E3, E2, 6k and E1.

4. The recombinant MVA of claim 1, wherein said third nucleotide sequence encodes a structural polyprotein comprising E3, E2, 6k and E1.

5. The recombinant MVA of claim 1, wherein each of said first, second, and third nucleotide sequence encodes a structural polyprotein comprising E3, E2, 6k, and E1.

6. The recombinant MVA of claim 2, wherein said first nucleotide sequence encoding a structural polyprotein of an Eastern equine encephalitis virus encodes an amino acid sequence comprising the sequence set forth in SEQ ID NO: 3.

7. The recombinant MVA of claim 3, wherein said second nucleotide sequence encoding a structural polyprotein of a Venezuelan equine encephalitis virus encodes an amino acid sequence comprising the sequence set forth in SEQ ID NO: 2.

8. The recombinant MVA of claim 4, wherein said third nucleotide sequence encoding a structural polyprotein of a Western equine encephalitis virus encodes an amino acid sequence comprising the sequence set forth in SEQ ID NO: 1.

9. The recombinant MVA of claim 5, wherein said first nucleotide sequence encodes an amino acid sequence comprising the sequence set forth in SEQ ID NO:3; said second nucleotide sequence encodes an amino acid sequence comprising the sequence set forth in SEQ ID NO:2; and said third nucleotide sequence encodes an amino acid sequence comprising the sequence set forth in SEQ ID NO: 1.

10. The recombinant MVA of claim 1, wherein said first nucleotide sequence encoding the structural polyprotein comprises the sequence set forth in SEQ ID NO: 4.

11. The recombinant MVA of claim 1, wherein said second nucleotide sequence encoding the structural polyprotein comprises the sequence set forth in SEQ ID NO: 5.

12. The recombinant MVA of claim 1, wherein said third nucleotide sequence encoding the structural polyprotein comprises the sequence set forth in SEQ ID NO: 6.

13. The recombinant MVA of claim 1, wherein said first nucleotide sequence encoding the structural polyprotein comprises the sequence set forth in SEQ ID NO: 4, said second nucleotide sequence encoding the structural polyprotein comprises the sequence set forth in SEQ ID NO: 5, and said third nucleotide sequence encoding the structural polyprotein comprises the sequence set forth in SEQ ID NO: 6.

14. The recombinant MVA of claim 1, wherein at least one of said promoters is selected from the group consisting of Pr13.5 and PrHyb.

15. The recombinant MVA of claim 1, wherein the MVA used for generating the recombinant MVA is MVA-BN as deposited at the European Collection of Animal Cell cultures under accession number V00083008.

16. The recombinant MVA of claim 15, wherein said first nucleotide sequence operably linked to a poxvirus promoter is inserted into the MVA intergenic region (IGR) 44/45.

17. The recombinant MVA of claim 16, wherein said second and third nucleotide sequences are inserted into the MVA intergenic region (IGR) 88/89.

18. A pharmaceutical composition comprising the recombinant MVA of claim 1 and a pharmaceutically acceptable carrier, excipient, or vehicle.

19. A vaccine comprising the recombinant MVA of claim 1.

20. A method for treating and/or preventing in a subject an equine encephalitis virus (EEV) caused disease comprising administering to the subject the recombinant modified vaccinia virus Ankara (MVA) of claim 1.

* * * * *

```
                      SEQUENCE LISTING

<160> NUMBER OF SEQ ID NOS: 8

<210> SEQ ID NO 1
<211> LENGTH: 978
<212> TYPE: PRT
<213> ORGANISM: Western equine encephalomyelitis virus

<400> SEQUENCE: 1

Met Ser Leu Val Thr Ala Leu Cys Val Leu Ser Asn Val Thr Phe Pro
1               5                   10                  15

Cys Asp Lys Pro Pro Val Cys Tyr Ser Leu Thr Pro Glu Arg Thr Leu
                20                  25                  30

Asp Val Leu Glu Glu Asn Val Asp Asn Pro Asn Tyr Asp Thr Leu Leu
            35                  40                  45

Glu Asn Val Leu Lys Cys Pro Ser Arg Arg Pro Lys Arg Ser Ile Thr
        50                  55                  60

Asp Asp Phe Thr Leu Thr Ser Pro Tyr Leu Gly Phe Cys Pro Tyr Cys
65                  70                  75                  80

Arg His Ser Thr Pro Cys Phe Ser Pro Ile Lys Ile Glu Asn Val Trp
                85                  90                  95

Asp Glu Ser Asp Asp Gly Ser Ile Arg Ile Gln Val Ser Ala Gln Phe
            100                 105                 110

Gly Tyr Asn Gln Ala Gly Thr Ala Asp Val Thr Lys Phe Arg Tyr Met
        115                 120                 125

Ser Phe Asp His Asp His Asp Ile Lys Glu Asp Ser Met Glu Lys Ile
    130                 135                 140

Ala Ile Ser Thr Ser Gly Pro Cys Arg Arg Leu Gly His Lys Gly Tyr
145                 150                 155                 160

Phe Leu Leu Ala Gln Cys Pro Pro Gly Asp Ser Val Thr Val Ser Ile
                165                 170                 175

Thr Ser Gly Ala Ser Glu Asn Ser Cys Thr Val Glu Lys Lys Ile Arg
            180                 185                 190

Arg Lys Phe Val Gly Arg Glu Glu Tyr Leu Phe Pro Pro Val His Gly
        195                 200                 205

Lys Leu Val Lys Cys His Val Tyr Asp His Leu Lys Glu Thr Ser Ala
    210                 215                 220
```

-continued

```
Gly Tyr Ile Thr Met His Arg Pro Gly Pro His Ala Tyr Lys Ser Tyr
225                 230                 235                 240

Leu Glu Glu Ala Ser Gly Glu Val Tyr Ile Lys Pro Pro Ser Gly Lys
            245                 250                 255

Asn Val Thr Tyr Glu Cys Lys Cys Gly Asp Tyr Ser Thr Gly Ile Val
        260                 265                 270

Ser Thr Arg Thr Lys Met Asn Gly Cys Thr Lys Ala Lys Gln Cys Ile
    275                 280                 285

Ala Tyr Lys Ser Asp Gln Thr Lys Trp Val Phe Asn Ser Pro Asp Leu
290                 295                 300

Ile Arg His Thr Asp His Ser Val Gln Gly Lys Leu His Ile Pro Phe
305                 310                 315                 320

Arg Leu Thr Pro Thr Val Cys Pro Val Pro Leu Ala His Thr Pro Thr
                325                 330                 335

Val Thr Lys Trp Phe Lys Gly Ile Thr Leu His Leu Thr Ala Met Arg
            340                 345                 350

Pro Thr Leu Leu Thr Thr Arg Lys Leu Gly Leu Arg Ala Asp Ala Thr
        355                 360                 365

Ala Glu Trp Ile Thr Gly Ser Thr Ser Arg Asn Phe Ser Val Gly Arg
370                 375                 380

Glu Gly Leu Glu Tyr Val Trp Gly Asn His Glu Pro Val Arg Val Trp
385                 390                 395                 400

Ala Gln Glu Ser Ala Pro Gly Asp Pro His Gly Trp Pro His Glu Ile
                405                 410                 415

Ile Ile His Tyr Tyr His Arg His Pro Val Tyr Thr Val Ile Val Leu
            420                 425                 430

Cys Gly Val Ala Leu Ala Ile Leu Val Gly Thr Ala Ser Ser Ala Ala
        435                 440                 445

Cys Ile Ala Lys Ala Arg Arg Asp Cys Leu Thr Pro Tyr Ala Leu Ala
    450                 455                 460

Pro Asn Ala Thr Val Pro Thr Ala Leu Ala Val Leu Cys Cys Ile Arg
465                 470                 475                 480

Pro Thr Asn Ala Glu Thr Phe Gly Glu Thr Leu Asn His Leu Trp Phe
                485                 490                 495

Asn Asn Gln Pro Phe Leu Trp Ala Gln Leu Cys Ile Pro Leu Ala Ala
            500                 505                 510

Leu Val Ile Leu Phe Arg Cys Phe Ser Cys Cys Met Pro Phe Leu Leu
        515                 520                 525

Val Ala Gly Val Cys Leu Gly Lys Val Asp Ala Phe Glu His Ala Thr
    530                 535                 540

Thr Val Pro Asn Val Pro Gly Ile Pro Tyr Lys Ala Leu Val Glu Arg
545                 550                 555                 560

Ala Gly Tyr Ala Pro Leu Asn Leu Glu Ile Thr Val Val Ser Ser Glu
                565                 570                 575

Leu Thr Pro Ser Thr Asn Lys Glu Tyr Val Thr Cys Lys Phe His Thr
            580                 585                 590

Val Ile Pro Ser Pro Gln Val Lys Cys Cys Gly Ser Leu Glu Cys Lys
        595                 600                 605

Ala Ser Ser Lys Ala Asp Tyr Thr Cys Arg Val Phe Gly Gly Val Tyr
    610                 615                 620

Pro Phe Met Trp Gly Gly Ala Gln Cys Phe Cys Asp Ser Glu Asn Thr
625                 630                 635                 640
```

```
Gln Leu Ser Glu Ala Tyr Val Glu Phe Ala Pro Asp Cys Thr Ile Asp
                645                 650                 655

His Ala Val Ala Leu Lys Val His Thr Ala Ala Leu Lys Val Gly Leu
            660                 665                 670

Arg Ile Val Tyr Gly Asn Thr Thr Ala His Leu Asp Thr Phe Val Asn
        675                 680                 685

Gly Val Thr Pro Gly Ser Ser Arg Asp Leu Lys Val Ile Ala Gly Pro
    690                 695                 700

Ile Ser Ala Ala Phe Ser Pro Phe Asp His Lys Val Val Ile Arg Lys
705                 710                 715                 720

Gly Leu Val Tyr Asn Tyr Asp Phe Pro Glu Tyr Gly Ala Met Lys Pro
                725                 730                 735

Gly Ala Phe Gly Asp Ile Gln Ala Ser Ser Leu Asp Ala Thr Asp Ile
            740                 745                 750

Val Ala Arg Thr Asp Ile Arg Leu Leu Lys Pro Ser Val Lys Asn Ile
        755                 760                 765

His Val Pro Tyr Thr Gln Ala Val Ser Gly Tyr Glu Met Trp Lys Asn
    770                 775                 780

Asn Ser Gly Arg Pro Leu Gln Glu Thr Ala Pro Phe Gly Cys Lys Ile
785                 790                 795                 800

Glu Val Glu Pro Leu Arg Ala Ser Asn Cys Ala Tyr Gly His Ile Pro
                805                 810                 815

Ile Ser Ile Asp Ile Pro Asp Ala Ala Phe Val Arg Ser Ser Glu Ser
            820                 825                 830

Pro Thr Ile Leu Glu Val Ser Cys Thr Val Ala Asp Cys Ile Tyr Ser
        835                 840                 845

Ala Asp Phe Gly Gly Ser Leu Thr Leu Gln Tyr Lys Ala Asp Arg Glu
    850                 855                 860

Gly His Cys Pro Val His Ser His Ser Thr Thr Ala Val Leu Lys Glu
865                 870                 875                 880

Ala Thr Thr His Val Thr Ala Val Gly Ser Ile Thr Leu His Phe Ser
                885                 890                 895

Thr Ser Ser Pro Gln Ala Asn Phe Ile Val Ser Leu Cys Gly Lys Lys
            900                 905                 910

Ser Thr Cys Asn Ala Glu Cys Lys Pro Pro Ala Asp His Ile Ile Gly
        915                 920                 925

Glu Pro His Lys Val Asp Gln Glu Phe Gln Ala Ala Val Ser Lys Thr
    930                 935                 940

Ser Trp Asn Trp Leu Leu Ala Leu Phe Gly Gly Ala Ser Ser Leu Ile
945                 950                 955                 960

Val Val Gly Leu Ile Val Leu Val Cys Ser Ser Met Leu Ile Asn Thr
                965                 970                 975

Arg Arg

<210> SEQ ID NO 2
<211> LENGTH: 981
<212> TYPE: PRT
<213> ORGANISM: Venezuelan equine encephalitis virus

<400> SEQUENCE: 2

Met Ser Leu Val Thr Thr Met Cys Leu Leu Ala Asn Val Thr Phe Pro
1               5                   10                  15

Cys Ala Gln Pro Pro Ile Cys Tyr Asp Arg Lys Pro Ala Glu Thr Leu
            20                  25                  30
```

-continued

```
Ala Met Leu Ser Val Asn Val Asp Asn Pro Gly Tyr Asp Glu Leu Leu
            35                  40                  45
Glu Ala Ala Val Lys Cys Pro Gly Arg Lys Arg Ser Thr Glu Glu
 50                  55                  60
Leu Phe Lys Glu Tyr Lys Leu Thr Arg Pro Tyr Met Ala Arg Cys Ile
 65                  70                  75                  80
Arg Cys Ala Val Gly Ser Cys His Ser Pro Ile Ala Ile Glu Ala Val
                     85                  90                  95
Lys Ser Asp Gly His Asp Gly Tyr Val Arg Leu Gln Thr Ser Ser Gln
                100                 105                 110
Tyr Gly Leu Asp Ser Ser Gly Asn Leu Lys Gly Arg Thr Met Arg Tyr
                115                 120                 125
Asp Met His Gly Thr Ile Lys Glu Ile Pro Leu His Gln Val Ser Leu
    130                 135                 140
His Thr Ser Arg Pro Cys His Ile Val Asp Gly His Gly Tyr Phe Leu
145                 150                 155                 160
Leu Ala Arg Cys Pro Ala Gly Asp Ser Ile Thr Met Glu Phe Lys Lys
                    165                 170                 175
Asp Ser Val Thr His Ser Cys Ser Val Pro Tyr Glu Val Lys Phe Asn
                    180                 185                 190
Pro Val Gly Arg Glu Leu Tyr Thr His Pro Pro Glu His Gly Val Glu
                    195                 200                 205
Gln Ala Cys Gln Val Tyr Ala His Asp Ala Gln Asn Arg Gly Ala Tyr
                    210                 215                 220
Val Glu Met His Leu Pro Gly Ser Glu Val Asp Ser Ser Leu Val Ser
225                 230                 235                 240
Leu Ser Gly Ser Ser Val Thr Val Thr Pro Pro Val Gly Thr Ser Ala
                    245                 250                 255
Leu Val Glu Cys Glu Cys Gly Gly Thr Lys Ile Ser Glu Thr Ile Asn
                    260                 265                 270
Lys Thr Lys Gln Phe Ser Gln Cys Thr Lys Lys Glu Gln Cys Arg Ala
                    275                 280                 285
Tyr Arg Leu Gln Asn Asp Lys Trp Val Tyr Asn Ser Asp Lys Leu Pro
            290                 295                 300
Lys Ala Ala Gly Ala Thr Leu Lys Gly Lys Leu His Val Pro Phe Leu
305                 310                 315                 320
Leu Ala Asp Gly Lys Cys Thr Val Pro Leu Ala Pro Glu Pro Met Ile
                    325                 330                 335
Thr Phe Gly Phe Arg Ser Val Ser Leu Lys Leu His Pro Lys Asn Pro
                    340                 345                 350
Thr Tyr Leu Thr Thr Arg Gln Leu Ala Asp Glu Pro His Tyr Thr His
                    355                 360                 365
Glu Leu Ile Ser Glu Pro Ala Val Arg Asn Phe Thr Val Thr Glu Lys
            370                 375                 380
Gly Trp Glu Phe Val Trp Gly Asn His Pro Pro Lys Arg Phe Trp Ala
385                 390                 395                 400
Gln Glu Thr Ala Pro Gly Asn Pro His Gly Leu Pro His Glu Val Ile
                    405                 410                 415
Thr His Tyr Tyr His Arg Tyr Pro Met Ser Thr Ile Leu Gly Leu Ser
                    420                 425                 430
Ile Cys Ala Ala Ile Ala Thr Val Ser Val Ala Ala Ser Thr Trp Leu
                    435                 440                 445
Phe Cys Arg Ser Arg Val Ala Cys Leu Thr Pro Tyr Arg Leu Thr Pro
```

```
                450             455             460
Asn Ala Arg Ile Pro Phe Cys Leu Ala Val Leu Cys Cys Ala Arg Thr
465                 470             475                 480

Ala Arg Ala Glu Thr Thr Trp Glu Ser Leu Asp His Leu Trp Asn Asn
            485                 490                 495

Asn Gln Gln Met Phe Trp Ile Gln Leu Leu Ile Pro Leu Ala Ala Leu
                500             505             510

Ile Val Val Thr Arg Leu Leu Arg Cys Val Cys Val Val Pro Phe
            515             520             525

Leu Val Met Ala Gly Ala Gly Ala Gly Ala Tyr Glu His Ala Thr
        530             535             540

Thr Met Pro Ser Gln Ala Gly Ile Ser Tyr Asn Thr Ile Val Asn Arg
545             550             555                 560

Ala Gly Tyr Ala Pro Leu Pro Ile Ser Ile Thr Pro Thr Lys Ile Lys
                565             570             575

Leu Ile Pro Thr Val Asn Leu Glu Tyr Val Thr Cys His Tyr Lys Thr
            580             585             590

Gly Met Asp Ser Pro Ala Ile Lys Cys Cys Gly Ser Gln Glu Cys Thr
        595             600             605

Pro Thr Tyr Arg Pro Asp Glu Gln Cys Lys Val Phe Thr Gly Val Tyr
        610             615             620

Pro Phe Met Trp Gly Gly Ala Tyr Cys Phe Cys Asp Thr Glu Asn Thr
625             630             635             640

Gln Val Ser Lys Ala Tyr Val Met Lys Ser Asp Asp Cys Leu Ala Asp
                645             650             655

His Ala Glu Ala Tyr Lys Ala His Thr Ala Ser Val Gln Ala Phe Leu
            660             665             670

Asn Ile Thr Val Gly Glu His Ser Ile Val Thr Thr Val Tyr Val Asn
            675             680             685

Gly Glu Thr Pro Val Asn Phe Asn Gly Val Lys Leu Thr Ala Gly Pro
        690             695             700

Leu Ser Thr Ala Trp Thr Pro Phe Asp Arg Lys Ile Val Gln Tyr Ala
705             710             715                 720

Gly Glu Ile Tyr Asn Tyr Asp Phe Pro Glu Tyr Gly Ala Gly Gln Pro
                725             730             735

Gly Ala Phe Gly Asp Ile Gln Ser Arg Thr Val Ser Ser Ser Asp Leu
            740             745             750

Tyr Ala Asn Thr Asn Leu Val Leu Gln Arg Pro Lys Ala Gly Ala Ile
            755             760             765

His Val Pro Tyr Thr Gln Ala Pro Ser Gly Phe Glu Gln Trp Lys Lys
        770             775             780

Asp Lys Ala Pro Ser Leu Lys Phe Thr Ala Pro Phe Gly Cys Glu Ile
785             790             795                 800

Tyr Thr Asn Pro Ile Arg Ala Glu Asn Cys Ala Val Gly Ser Ile Pro
                805             810             815

Leu Ala Phe Asp Ile Pro Asp Ala Leu Phe Thr Arg Val Ser Glu Thr
            820             825             830

Pro Thr Leu Ser Ala Ala Glu Cys Thr Leu Asn Glu Cys Val Tyr Ser
        835             840             845

Ser Asp Phe Gly Gly Ile Ala Thr Val Lys Tyr Ser Ala Ser Lys Ser
        850             855             860

Gly Lys Cys Ala Val His Val Pro Ser Gly Thr Ala Thr Leu Lys Glu
865             870             875             880
```

```
Ala Ala Val Glu Leu Thr Glu Gln Gly Ser Ala Thr Ile His Phe Ser
            885                 890                 895

Thr Ala Asn Ile His Pro Glu Phe Arg Leu Gln Ile Cys Thr Ser Tyr
            900                 905                 910

Val Thr Cys Lys Gly Asp Cys His Pro Pro Lys Asp His Ile Val Thr
            915                 920                 925

His Pro Gln Tyr His Ala Gln Thr Phe Thr Ala Val Ser Lys Thr
            930                 935                 940

Ala Trp Thr Trp Leu Thr Ser Leu Leu Gly Gly Ser Ala Val Ile Ile
945                 950                 955                 960

Ile Ile Gly Leu Val Leu Ala Thr Ile Val Ala Met Tyr Val Leu Thr
            965                 970                 975

Asn Gln Lys His Asn
            980

<210> SEQ ID NO 3
<211> LENGTH: 982
<212> TYPE: PRT
<213> ORGANISM: Eastern equine encephalomyelitis virus

<400> SEQUENCE: 3

Met Ser Leu Ala Thr Val Met Cys Val Leu Ala Asn Ile Thr Phe Pro
1               5                   10                  15

Cys Asp Gln Pro Pro Cys Met Pro Cys Cys Tyr Glu Lys Asn Pro His
            20                  25                  30

Glu Thr Leu Thr Met Leu Glu Gln Asn Tyr Asp Ser Arg Ala Tyr Asp
            35                  40                  45

Gln Leu Leu Asp Ala Ala Val Lys Cys Asn Ala Arg Arg Thr Arg Arg
        50                  55                  60

Asp Leu Asp Thr His Phe Thr Gln Tyr Lys Leu Ala Arg Pro Tyr Ile
65              70                  75                  80

Ala Asp Cys Pro Asn Cys Gly His Ser Arg Cys Asp Ser Pro Ile Ala
            85                  90                  95

Ile Glu Glu Val Arg Gly Asp Ala His Ala Gly Val Ile Arg Ile Gln
            100                 105                 110

Thr Ser Ala Met Phe Gly Leu Lys Thr Asp Gly Val Asp Leu Ala Tyr
            115                 120                 125

Met Ser Phe Met Asn Gly Lys Thr Gln Lys Ser Ile Lys Ile Asp Asn
            130                 135                 140

Leu His Val Arg Thr Ser Ala Pro Cys Ser Leu Val Ser His His Gly
145                 150                 155                 160

Tyr Tyr Ile Leu Ala Gln Cys Pro Pro Gly Asp Thr Val Thr Val Gly
            165                 170                 175

Phe His Asp Gly Pro Asn Arg His Thr Cys Thr Val Ala His Lys Val
            180                 185                 190

Glu Phe Arg Pro Val Gly Arg Glu Lys Tyr Arg His Pro Pro Glu His
            195                 200                 205

Gly Val Glu Leu Pro Cys Asn Arg Tyr Thr His Lys Arg Ala Asp Gln
            210                 215                 220

Gly His Tyr Val Glu Met His Gln Pro Gly Leu Val Ala Asp His Ser
225                 230                 235                 240

Leu Leu Ser Ile His Ser Ala Lys Val Lys Ile Thr Val Pro Ser Gly
            245                 250                 255

Ala Gln Val Lys Tyr Tyr Cys Lys Cys Pro Asp Val Arg Glu Gly Ile
```

```
                260                 265                 270
Thr Ser Ser Asp His Thr Thr Thr Cys Thr Asp Val Lys Gln Cys Arg
            275                 280                 285
Ala Tyr Leu Ile Asp Asn Lys Lys Trp Val Tyr Asn Ser Gly Arg Leu
        290                 295                 300
Pro Arg Gly Glu Gly Asp Thr Phe Lys Gly Lys Leu His Val Pro Phe
305                 310                 315                 320
Val Pro Val Lys Ala Lys Cys Ile Ala Thr Leu Ala Pro Glu Pro Leu
                325                 330                 335
Val Glu His Lys His Arg Thr Leu Ile Leu His Leu His Pro Asp His
            340                 345                 350
Pro Thr Leu Leu Thr Thr Arg Ser Leu Gly Ser Asp Ala Asn Pro Thr
        355                 360                 365
Arg Gln Trp Ile Glu Arg Pro Thr Thr Val Asn Phe Thr Val Thr Gly
    370                 375                 380
Glu Gly Leu Glu Tyr Thr Trp Gly Asn His Pro Pro Lys Arg Val Trp
385                 390                 395                 400
Ala Gln Glu Ser Gly Glu Gly Asn Pro His Gly Trp Pro His Glu Val
                405                 410                 415
Val Val Tyr Tyr Tyr Asn Arg Tyr Pro Leu Thr Thr Ile Ile Gly Leu
            420                 425                 430
Cys Thr Cys Val Ala Ile Ile Met Val Ser Cys Val Thr Ser Val Trp
        435                 440                 445
Leu Leu Cys Arg Thr Arg Asn Leu Cys Ile Thr Pro Tyr Lys Leu Ala
    450                 455                 460
Pro Asn Ala Gln Val Pro Ile Leu Leu Ala Leu Leu Cys Cys Ile Lys
465                 470                 475                 480
Pro Thr Arg Ala Asp Asp Thr Leu Gln Val Leu Asn Tyr Leu Trp Asn
                485                 490                 495
Asn Asn Gln Asn Phe Phe Trp Met Gln Thr Leu Ile Pro Leu Ala Ala
            500                 505                 510
Leu Ile Val Cys Met Arg Met Leu Arg Cys Leu Phe Cys Cys Gly Pro
        515                 520                 525
Ala Phe Leu Leu Val Cys Gly Ala Leu Gly Ala Ala Ala Tyr Glu His
    530                 535                 540
Thr Ala Val Met Pro Asn Lys Val Gly Ile Pro Tyr Lys Ala Leu Val
545                 550                 555                 560
Glu Arg Pro Gly Tyr Ala Pro Val His Leu Gln Ile Gln Leu Val Asn
                565                 570                 575
Thr Arg Ile Ile Pro Ser Thr Asn Leu Glu Tyr Ile Thr Cys Lys Tyr
            580                 585                 590
Lys Thr Lys Val Pro Ser Pro Val Lys Cys Cys Gly Ala Thr Gln
        595                 600                 605
Cys Thr Ser Lys Pro His Pro Asp Tyr Gln Cys Gln Val Phe Thr Gly
    610                 615                 620
Val Tyr Pro Phe Met Trp Gly Gly Ala Tyr Cys Phe Cys Asp Thr Glu
625                 630                 635                 640
Asn Thr Gln Met Ser Glu Ala Tyr Val Glu Arg Ser Glu Glu Cys Ser
                645                 650                 655
Ile Asp His Ala Lys Ala Tyr Lys Val His Thr Gly Thr Val Gln Ala
            660                 665                 670
Met Val Asn Ile Thr Tyr Gly Ser Val Ser Trp Arg Ser Ala Asp Val
        675                 680                 685
```

Tyr Val Asn Gly Glu Thr Pro Ala Lys Ile Gly Asp Ala Lys Leu Ile
690                 695                 700

Ile Gly Pro Leu Ser Ser Ala Trp Ser Pro Phe Asp Asn Lys Val Val
705                 710                 715                 720

Val Tyr Gly His Glu Val Tyr Asn Tyr Asp Phe Pro Glu Tyr Gly Thr
            725                 730                 735

Gly Lys Ala Gly Ser Phe Gly Asp Leu Gln Ser Arg Thr Ser Thr Ser
            740                 745                 750

Asn Asp Leu Tyr Ala Asn Thr Asn Leu Lys Leu Gln Arg Pro Gln Ala
            755                 760                 765

Gly Ile Val His Thr Pro Phe Thr Gln Ala Pro Ser Gly Phe Glu Arg
770                 775                 780

Trp Lys Arg Asp Lys Gly Ala Pro Leu Asn Asp Val Ala Pro Phe Gly
785                 790                 795                 800

Cys Ser Ile Ala Leu Glu Pro Leu Arg Ala Glu Asn Cys Ala Val Gly
            805                 810                 815

Ser Ile Pro Ile Ser Ile Asp Ile Pro Asp Ala Ala Phe Thr Arg Ile
            820                 825                 830

Ser Glu Thr Pro Thr Val Ser Asp Leu Glu Cys Lys Ile Thr Glu Cys
            835                 840                 845

Thr Tyr Ala Ser Asp Phe Gly Gly Ile Ala Thr Val Ala Tyr Lys Ser
850                 855                 860

Ser Lys Ala Gly Asn Cys Pro Ile His Ser Pro Ser Gly Val Ala Val
865                 870                 875                 880

Ile Lys Glu Asn Asp Val Thr Leu Ala Glu Ser Gly Ser Phe Thr Phe
            885                 890                 895

His Phe Ser Thr Ala Asn Ile His Pro Ala Phe Lys Leu Gln Val Cys
            900                 905                 910

Thr Ser Ala Val Thr Cys Lys Gly Asp Cys Lys Pro Pro Lys Asp His
            915                 920                 925

Ile Val Asp Tyr Pro Ala Gln His Thr Glu Ser Phe Thr Ser Ala Ile
930                 935                 940

Ser Ala Thr Ala Trp Ser Trp Leu Lys Val Leu Val Gly Gly Thr Ser
945                 950                 955                 960

Ala Phe Ile Val Leu Gly Leu Ile Ala Thr Ala Val Val Ala Leu Val
            965                 970                 975

Leu Phe Phe His Arg His
            980

<210> SEQ ID NO 4
<211> LENGTH: 2934
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: synthetic

<400> SEQUENCE: 4
atgagcctcg tgaccgccct gtgtgtgctg agcaacgtga cattcccctg cgacaagcct      60
cccgtgtgct acagcctgac acccgagaga accctggacg tgctggaaga gaatgtggac     120
aaccccaact acgatccct gctggaaaac gtgctgaaat gccccagcag acggcccaag      180
cggagcatca ccgacgattt caccctgacc tctccctacc tgggcttctg ccctactgc      240

-continued

```
aggcactcca ctccttgctt cagccccatt aagatcgaga acgtgtggga cgagagcgac    300
gacggcagca tcaggatcca ggtgtccgcc cagttcggct acaaccaggc tggcaccgcc    360
gatgtgacca agttccggta catgtccttc gaccacgacc acgatatcaa agaggacagc    420
atggaaaaga tcgccatctc caccagcggt ccctgcaggc ggctgggcca aagggctac     480
tttctgctgg ctcagtgtcc tccaggcgat agcgtgacag tgtccatcac ctctggagcc    540
agcgagaaca gctgcaccgt ggaaaagaag atcagacgga agttcgtggg cagagaagag    600
tacctgttcc cacctgtgca cggcaagctc gtgaagtgtc acgtgtacga ccacctgaaa    660
gagacaagcg ctggctatat caccatgcac agacccggac ctcacgccta caagtcctac    720
ctggaagagg ccagcggcga agtgtacatc aagccaccct ccggcaagaa cgtgacctac    780
gagtgcaagt gcggcgacta cagcacaggc atcgtgtcca cccggaccaa gatgaacggc    840
tgcaccaagg ccaagcagtg tattgcctat aagagcgacc agaccaaatg ggtcttcaac    900
tctcctgacc tgatcagaca caccgaccac tccgtgcagg aaaactgca catcccttc     960
cggctgaccc ctaccgtgtg ccctgtgcct ctggcccaca ccccaaccgt gacaaagtgg   1020
ttcaagggaa tcaccctgca cctgaccgcc atgcggccta cactgctgac aacccggaag   1080
ctgggcctga gagccgatgc caccgccgag tggatcaccg gcagcacctc ccggaacttc   1140
tctgtgggca gggaaggcct ggaatacgtg tggggcaatc acgagcccgt ccgcgtctgg   1200
gctcaggaat ctgccccagg cgatccccac ggctggcctc acgaaatcat catccactac   1260
taccacaggc accccgtgta cacagtgatc gtgctgtgtg cgtggcact  ggccatcctc   1320
gtgggcacag ccagctctgc cgcctgtatt gccaaggcca ggcgggactg tctgacgcct   1380
tacgccctgg ctcccaatgc caccgtgcct accgctctgg ccgtcctgtg ttgcatccgg   1440
cctaccaacg ccgagacatt cggcgaaacc ctgaatcacc tgtggttcaa caatcagccc   1500
ttcctgtggg ctcagctgtg catcccactg ctgccctcg tgatcctgtt cagatgcttc    1560
agctgctgta tgccttttcct gctggtggct ggcgtgtgcc tgggcaaggt ggacgccttt   1620
gagcacgcca caccgtgcc caacgtgccc ggaatcccct acaaagctct ggtcgagagg   1680
gctggatacg cccctctgaa cctggaaatc accgtggtgt ccagcgagct gaccccaagc   1740
accaacaaag aatacgtgac ctgtaaattc cacaccgtga tccccagccc tcaggtcaag   1800
tgttgtggca gcctggaatg taaagccagc tccaaggccg actacacctg tcgggtgttc   1860
ggcggagtgt atccttttat gtggggaggt gcccagtgct tttgtgatag cgagaatacc   1920
cagctgtctg aggcctatgt ggaattcgct cccgactgta ccatcgacca tgccgtggcc   1980
ctgaaagtgc acacagccgc actgaaagtg gcctgcggaa tcgtgtacgg caataccacc   2040
gcccacctgg ataccttcgt gaatggcgtg acacccggca gcagccggga tctgaaagtg   2100
atcgccggac ccatctccgc cgcctttagc cctttcgacc acaaggtcgt gatccgcaag   2160
ggcctggtgt acaattatga ttttcctgaa tacggagcca tgaagcctgg cgccttcggc   2220
gacatccagg ccagctccct ggatgccaca gacatcgtgg ctcggaccga catcagactg   2280
ctgaagccca gcgtgaagaa catccacgtg ccatacaccc aggccgtgtc tggctacgag   2340
atgtggaaga caatagcgg caggccactg caggaaaccg ccccttcgg ctgcaagatc    2400
gaggtggaac ctctgagagc cagcaactgc gcctacggcc atatccccat ctctatcgat   2460
attccagatg ccgccttcgt gcggagcagc gagtctccta ccatcctgga agtgtcctgc   2520
actgtggccg actgtatcta cagcgccgat ttcggaggct ccctgaccct gcagtacaag   2580
gccgatagag agggccactg ccccgtgcac tctcacagca ccaccgcagt gctgaaagag   2640
```

-continued

```
gccaccacac acgtcaccgc cgtcggctcc atcacactgc actttagcac cagctcccca    2700
caggccaact tcattgtgtc cctgtgcggc aagaagtcca cctgtaacgc cgagtgcaaa    2760
ccacctgccg atcacatcat cggagagccc cataaggtgg accaggaatt ccaggcagcc    2820
gtcagcaaga cctcctggaa ctggctgctg cactgttcg gaggcgccag ctctctgatc    2880
gtcgtgggcc tgatcgtcct cgtgtgcagc tccatgctga tcaatactcg gaga          2934
```

<210> SEQ ID NO 5
<211> LENGTH: 2943
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: synthetic

<400> SEQUENCE: 5

```
atgtccctgg tcacaactat gtgcctcctg gccaatgtga cctttccatg tgctcagcca      60
cctatctgtt acgaccggaa gcctgccgaa actctcgcca tgctgagcgt gaacgtggat     120
aatccaggct atgatgagct gctcgaggct gccgtcaagt gtcccggcag aaagcggaga     180
agcaccgagg aactgttcaa agagtataag ctgacaagac cttatatggc tcggtgcatc     240
agatgtgccg tgggctcttg ccactcccca atcgccattg aggctgtgaa gtccgacgga     300
cacgatggct acgtgcggct gcagacctcc agccagtacg gactggacag cagcggcaac     360
ctgaagggac ggaccatgag atacgacatg cacggcacca tcaaggaaat ccctctgcat     420
caggtgtccc tgcacaccct cagaccatgt cacattgtgg acggccacgg atatttcctg     480
ctcgcacggt gccctgccgg agactccatc accatggaat tcaagaaaga ctccgtgacc     540
cactcctgta gcgtgcccta cgaagtgaag ttcaaccctg tggggcggga gctgtacaca     600
caccctccag aacacggagt cgagcaggcc tgtcaggtct atgctcacga cgcccagaac     660
agaggcgcct atgtcgagat gcacctccct ggctccgagg tggacagttc cctggtgtct     720
ctgagcggct cctctgtgac cgtgaccccc ccagtgggca aagcgccct cgtggaatgc     780 gagtgtggag gcaccaagat cagcgagaca atcaacaaga caaagcagtt cagccagtgt     840
acaaagaaag agcaatgtcg ggcctacaga ctgcagaacg ataagtgggt gtacaatagc     900
gacaagctgc ctaaggccgc aggcgccaca ctgaaaggca agctgcatgt gccattcctc     960
ctcgccgacg gcaaatgcac agtgccactc gctcctgaac ccatgatcac cttcggcttc    1020
agaagcgtgt ccctgaagct ccaccccaag aaccccacct acctgaccac aagacagctg    1080
gccgacgagc ccactacac ccacgagctg atctctgagc cagccgtgag aaacttcaca    1140
gtgaccgaga agggctggga gttcgtctgg ggaaaccatc ctcctaagcg gttttgggca    1200
caggagacag ctcccggcaa tccacatgga ctgccacacg aggtgattac ccattactat    1260
catcgctacc caatgagcac aatcctgggc ctgtccatct gtgccgccat tgccactgtg    1320
tcagtggctg ccagcacctg gctgttctgc cggtccagag tggcctgcct gacaccatac    1380
cggctgactc ctaacgccag gatccccttt gcctggcag tgctctgctg tgccagaacc    1440
gccagggcag aaacaacctg ggagtctctg gaccacctct ggaacaataa ccagcagatg    1500
ttttggatcc agctcctgat tcctctggca gctctgattg tggtcacacg gctgctgcgg    1560
tgcgtgtgct gcgtggtgcc cttcctcgtg atggcaggag cagccggagc aggcgcttac    1620
gagcatgcca ccacaatgcc tagccaggct ggaattagct acaacaccat cgtgaacaga    1680
```

```
gccggctatg ctccactgcc catctccatt acacctacca agattaagct gatccctacc      1740
gtgaacctcg agtatgtgac atgccactac aagaccggca tggacagccc agccatcaaa      1800
tgctgcggat cccaggagtg caccccaacc tacagacccg atgagcagtg taaagtgttt      1860
acaggcgtct acccattcat gtggggtggc gcttactgtt tctgcgacac agagaacact      1920
caggtcagca aagcctacgt gatgaagtct gacgattgtc tggccgatca cgctgaggcc      1980
tataaggccc ataccgcttc tgtgcaggcc tttctgaaca tcacagtggg cgagcactcc      2040
atcgtgacca cagtgtatgt gaacggggag actcctgtga atttcaacgg cgtgaagctg      2100
acagctggac cactgagcac tgcctggaca cccttcgata gaaagatcgt gcagtacgct      2160
ggcgagatct ataactacga cttcccagag tatggcgcag ccagccagg gcatttgga       2220 gatattcaga gcagaaccgt gtccagctcc gatctgtatg ccaataccaa tctggtgctc      2280
cagagaccta aggctggcgc catccatgtg ccctatactc aggctccatc tggatttgag      2340
cagtggaaga aggataaggc ccctagcctg aagttcacag ctcccttcgg atgcgaaatc      2400
tacaccaacc ctatcagagc cgagaactgt gctgtgggat ccatccctct ggccttcgac      2460
atccccgacg ccctgttcac cagagtgtcc gaaaccccta ccctgagcgc agctgagtgc      2520
accctgaatg agtgcgtgta ctccagcgac tttggcggaa tcgctacagt gaagtacagc      2580
gcctccaagt ccggcaagtg cgccgtccac gtcccaagcg gcaccgccac tctcaaggag      2640
gcagccgtcg agctgacaga gcagggcagc gccacaatcc acttctccac agccaatatt      2700
caccccgagt tccggctcca gatctgcacc tcctacgtga catgcaaagg ggattgccac      2760
cctccaaagg accatatcgt gactcaccct cagtaccacg cccagacctt cactgctgcc      2820
gtgtctaaga cagcctggac atggctgaca tccctgctgg gcggaagcgc tgtgatcatt      2880
ataatcggcc tggtgctcgc cactatcgtg gctatgtacg tgctgaccaa ccagaaacac      2940
aac                                                                   2943

<210> SEQ ID NO 6
<211> LENGTH: 2946
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: synthetic

<400> SEQUENCE: 6
atgagcctgg ccaccgtgat gtgcgtgctg gccaacatca ccttcccatg cgaccagcca       60
ccttgcatgc cctgctgcta cgagaagaac ccacacgaga cactgaccat gctggaacag      120
aactacgaca gcagagccta cgaccagctg ctggacgctg ccgtgaagtg caacgccaga      180
cggaccagac gggacctgga cacccacttc acccagtaca agctggccag accctatatc      240
gccgactgcc caactgcgg ccacagcaga tgcgacagcc tatcgccat cgaggaagtg       300 agaggcgacg cccatgctgg cgtgatcaga atccagacca cgccatgtt cggcctgaaa      360 accgacggcg tggacctggc ctacatgagc ttcatgaacg gcaagaccca gaagtccatc      420
aagatcgaca acctgcacgt gcggacctcc gctccctgta gcctggtgtc ccaccacggc      480
tactacatcc tggcccagtg ccctcctggc gacaccgtga ccgtgggctt ccacgacgga      540
cccaaccgga cacctgtac cgtggcccac aaggtggaat tcagacccgt gggcagagag      600
aagtaccggc accctcccga gcacggggtg gaactgccct gcaaccggta cacccacaag      660
```

| | |
|---|---|
| cgggcagacc agggccacta cgtggaaatg catcagcctg gcctggtggc cgaccacagc | 720 |
| ctgctgagca tccacagcgc caaagtgaag atcaccgtgc cctctggagc ccaggtcaaa | 780 |
| tattactgca agtgccccga cgtgcgcgag ggcatcacca gcagcgacca caccaccaca | 840 |
| tgcaccgacg tgaagcagtg cagagcctac ctgatcgata caagaaatg gtgtacaac | 900 |
| agcggcagac tgcccagagg cgagggcgac accttcaagg gcaagctcca cgtccccttc | 960 |
| gtgcccgtga aggccaagtg tatcgccacc ctggcccctg agccactggt ggaacacaag | 1020 |
| caccggaccc tgatcctgca tctgcacccc gaccacccca ccctgctgac cacaagaagc | 1080 |
| ctgggcagcg acgccaaccc tacccggcag tggatcgaga ggccaccac cgtgaacttt | 1140 |
| accgtgactg gcgagggcct cgagtacacc tggggcaacc accctcccaa gagagtgtgg | 1200 |
| gcccaggaaa gcggcgaggg caaccctcac ggatggcccc acgaggtggt ggtctactac | 1260 |
| tacaacagat acccactgac caccatcatc ggcctgtgca cctgtgtggc catcatcatg | 1320 |
| gtgtcctgcg tgaccagcgt gtggctgctg tgcagaaccc ggaacctgtg catcacaccc | 1380 |
| tataagctgg cacccaacgc ccaggtgccc atcctgctcg ctctgctctg ctgcatcaag | 1440 |
| cccaccagag ccgacgacac cctgcaggtc ctgaactacc tgtggaacaa caaccagaac | 1500 |
| ttcttctgga tgcagacact gatccctctg gcagccctga tcgtgtgcat gcggatgctg | 1560 |
| cggtgcctgt tctgctgcgg acctgccttc tgctcgtgt gcggagccct gggagccgct | 1620 |
| gcctatgagc acacagccgt gatgcccaac aaagtgggca tcccttacaa ggcactggtg | 1680 |
| gaaagacccg gctacgcacc cgtccacctc cagatccagc tggtcaacac ccggatcatc | 1740 |
| cccagcacca atctcgagta tatcacctgt aagtataaga ccaaggtgcc tagccccgtg | 1800 |
| gtcaagtgct gcgagccac ccagtgcacc agcaagcctc accccgacta ccagtgccag | 1860 |
| gtgttcaccg gcgtgtaccc ctttatgtgg ggtggagcct actgcttctg cgacaccgag | 1920 |
| aacacccaga tgagcgaggc ctacgtcgag cggagcgagg aatgcagcat cgaccacgcc | 1980 |
| aaggcttaca aggtgcacac cggcaccgtg caggccatgg tcaatatcac ctacggcagc | 2040 |
| gtgtcctggc ggagtgccga cgtgtacgtg aacggcgaga cacccgccaa gatcggggac | 2100 |
| gccaagctga tcatcggacc cctgtctagc gcctggtccc catttgacaa caaagtcgtg | 2160 |
| gtgtacggcc acgaggtcta caactatgac ttccccgagt acggcaccgg caaggctggc | 2220 |
| agctttggcg acctgcagag ccggaccagc acaagcaacg acctgtacgc caacaccaac | 2280 |
| ctgaagctgc agaggcctca ggcaggcatc gtgcacaccc cttttacaca ggctcccagc | 2340 |
| ggcttcgagc ggtggaagag agacaagggc gctcccctga cgacgtggc tcccttcgga | 2400 |
| tgctctatcg ccctggaacc cctgagagcc gagaattgcg cagtgggcag catccccatc | 2460 |
| agcattgaca tccctgacgc agccttcacc agaatctccg agactcccac cgtgtccgac | 2520 |
| ctggaatgca agatcacaga gtgcacctac gcctccgact tcggagggat cgccacagtg | 2580 |
| gcctacaaaa gctccaaagc cggcaactgc cccatccaca gtcccagcgg cgtggccgtg | 2640 |
| atcaaagaaa acgacgtgac cctggccgag agcggcagct tcaccttcca cttcagcacc | 2700 |
| gccaacatcc accctgcatt caagctgcag gtctgcacca cgccgtgac ctgcaagggc | 2760 |
| gactgcaagc ctcccaagga ccacatcgtg gactaccctg cccagcacac cgagagcttt | 2820 |
| acctccgcca tcagcgccac cgcttggtct tggctgaagg tgctcgtggg aggcacctct | 2880 |
| gccttcatcg tgctcggact gatcgccact gccgtggtcg ccctggtgct gttctttcac | 2940 |
| cggcac | 2946 |

```
<210> SEQ ID NO 7
<211> LENGTH: 124
<212> TYPE: DNA
<213> ORGANISM: Artificial sequence
<220> FEATURE:
<223> OTHER INFORMATION: synthetic

<400> SEQUENCE: 7
taaaaataga aactataatc atataatagt gtaggttggt agtattgctc ttgtgactag        60
agactttagt taaggtactg taaaaataga aactataatc atataatagt gtaggttggt       120
agta                                                                    124

<210> SEQ ID NO 8
<211> LENGTH: 227
<212> TYPE: DNA
<213> ORGANISM: Artificial sequence
<220> FEATURE:
<223> OTHER INFORMATION: synthetic

<400> SEQUENCE: 8
gttttgaaaa ttttttata ataaatatcc ggtaaaaatt gaaaaactat tctaatttat         60
tgcacggtcc ggtaaaaatt gaaaaactat tctaatttat tgcacggtcc ggtaaaaatt       120
gaaaaactat tctaatttat tgcacggtcc ggtaaaaatt gaaaaactat tctaatttat       180
tgcacggtcc ggtaaaaatt gaaaaactat tctaatttat tgcacgg                    227
```